(12) United States Patent
Yesudas et al.

(10) Patent No.: US 12,419,929 B2
(45) Date of Patent: Sep. 23, 2025

(54) COMPOSITIONS OF HERBAL FORMULATIONS AND USES THEREOF

(71) Applicant: HAUS BIOCEUTICALS, INC., Oklahoma City, OK (US)

(72) Inventors: Tomy Yesudas, Kollam Kerala (IN); Philip Alex, Abingdon, MD (US); Michael Centola, Oklahoma City, OK (US); Adam Joshua Payne, Edmond, OK (US)

(73) Assignee: Haus Bioceuticals, Inc., Oklahoma City, OK (US)

( * ) Notice: Subject to any disclaimer, the term of this patent is extended or adjusted under 35 U.S.C. 154(b) by 0 days.

(21) Appl. No.: 18/659,701

(22) Filed: May 9, 2024

(65) Prior Publication Data

US 2024/0285721 A1 Aug. 29, 2024

Related U.S. Application Data

(63) Continuation of application No. 17/684,811, filed on Mar. 2, 2022, now abandoned, which is a continuation of application No. 16/842,528, filed on Apr. 7, 2020, now abandoned, which is a continuation of application No. 15/889,921, filed on Feb. 6, 2018, now abandoned, which is a continuation of application No. 14/733,771, filed on Jun. 8, 2015, now Pat. No. 9,889,174, which is a continuation of application No. 13/471,913, filed on May 15, 2012, now Pat. No. 9,050,359.

(60) Provisional application No. 61/486,724, filed on May 16, 2011.

(51) Int. Cl.
| | |
|---|---|
| *A61K 36/00* | (2006.01) |
| *A61K 36/185* | (2006.01) |
| *A61K 36/22* | (2006.01) |
| *A61K 36/23* | (2006.01) |
| *A61K 36/24* | (2006.01) |
| *A61K 36/27* | (2006.01) |
| *A61K 36/28* | (2006.01) |
| *A61K 36/29* | (2006.01) |
| *A61K 36/31* | (2006.01) |
| *A61K 36/35* | (2006.01) |
| *A61K 36/48* | (2006.01) |
| *A61K 36/66* | (2006.01) |
| *A61K 36/68* | (2006.01) |
| *A61K 36/71* | (2006.01) |
| *A61K 36/76* | (2006.01) |
| *A61K 36/77* | (2006.01) |
| *A61K 36/808* | (2006.01) |
| *A61K 36/899* | (2006.01) |
| *A61K 36/90* | (2006.01) |

(52) U.S. Cl.
CPC ............ *A61K 36/90* (2013.01); *A61K 36/185* (2013.01); *A61K 36/22* (2013.01); *A61K 36/23* (2013.01); *A61K 36/24* (2013.01); *A61K 36/27* (2013.01); *A61K 36/28* (2013.01); *A61K 36/29* (2013.01); *A61K 36/31* (2013.01); *A61K 36/35* (2013.01); *A61K 36/48* (2013.01); *A61K 36/66* (2013.01); *A61K 36/68* (2013.01); *A61K 36/71* (2013.01); *A61K 36/76* (2013.01); *A61K 36/77* (2013.01); *A61K 36/808* (2013.01); *A61K 36/899* (2013.01)

(58) Field of Classification Search
CPC ......... A61K 36/90; A61K 36/28; A61K 36/29
See application file for complete search history.

(56) References Cited

FOREIGN PATENT DOCUMENTS

JP 2002047132 A * 2/2002

* cited by examiner

*Primary Examiner* — Qiuwen Mi

(74) *Attorney, Agent, or Firm* — Dunlap Codding, P.C.

(57) ABSTRACT

Disclosed herein are herbal formulations for relief from symptoms of skin disease. The formulations can also be combined with an active or inactive pharmaceutical ingredient, and/or a pharmaceutically acceptable excipient.

12 Claims, 4 Drawing Sheets

COMPOSITIONS OF HERBAL FORMULATIONS AND USES THEREOF

CROSS REFERENCE TO RELATED APPLICATIONS/INCORPORATION BY REFERENCE

This application is a continuation of U.S. patent application Ser. No. 17/684,811, filed Mar. 2, 2022, now abandoned; which is a continuation of U.S. patent application Ser. No. 16/842,528, filed Apr. 7, 2020, now abandoned; which is a continuation of U.S. patent application Ser. No. 15/889,921, filed Feb. 6, 2018, now abandoned; which is a continuation of U.S. patent application Ser. No. 14/733,771, filed Jun. 8, 2015, now U.S. Pat. No. 9,889,174, issued Feb. 13, 2018; which is a continuation of U.S. patent application Ser. No. 13/471,913, filed May 15, 2012, now U.S. Pat. No. 9,050,359, issued Jun. 9, 2015; which claims priority under 35 USC § 119(e) to U.S. Provisional Application No. 61/486,724, filed May 16, 2011. The entire contents of each of the above-referenced patent applications are hereby expressly incorporated herein by reference.

BACKGROUND

Human bodies have evolved over millions of years in harmony with nature. Certain natural products induce the human body to function more efficiently at combating disease and adverse conditions. These products help the human body heal itself. Skin conditions, the most visible of human maladies, have historically received the most attention when it comes to the application of herbal remedies. Herbs have been used in the healing of adverse skin conditions for thousands of years. Aloe vera, for example, is an herbal extract that has been used throughout history as a skin soothant and healant. Even today, lotions containing aloe vera are used to help skin to heal after sunburn.

Despite advances in science, skin conditions remain prevalent and the alleviation of symptoms remains elusive. Humans must return to nature from whence they came to find suitable relief for these conditions.

DETAILED DESCRIPTION

Figure 1:
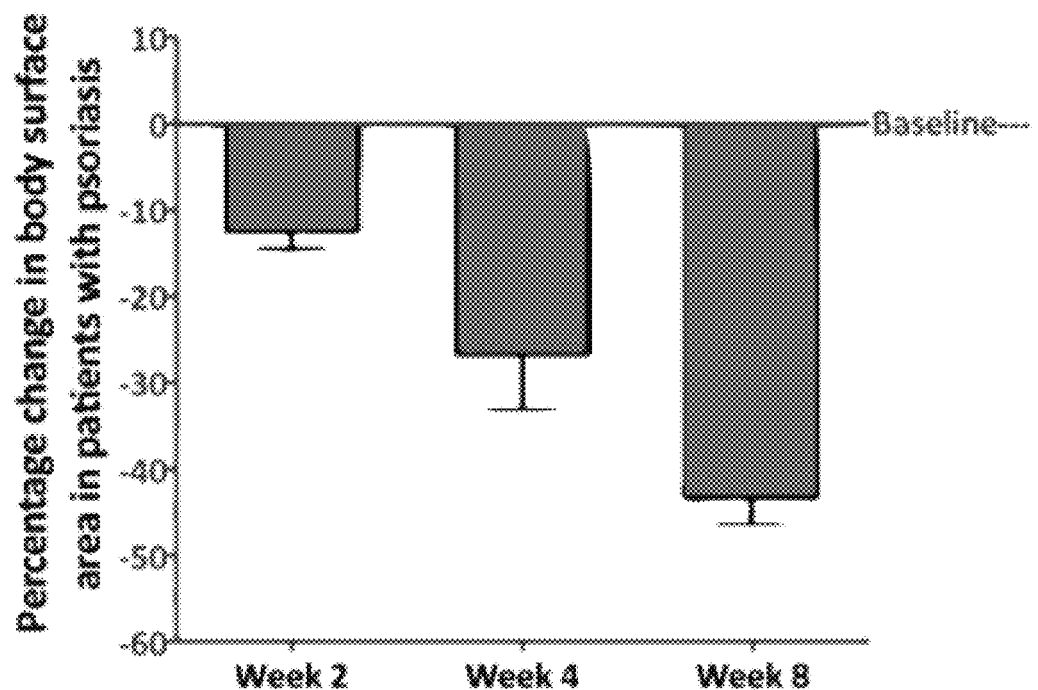
FIG. 1 is a graph showing the results of the application of the HAT-01 formulation to psoriasis patients.

Disclosed herein are herbal compositions, based on a proprietary preparation of traditional commonly used herbs. Our studies have demonstrated that these formulations are potent and safe agents with benefit in aiding the body to alleviate the symptoms of chronic skin conditions as described herein.

Disclosed herein are compositions comprising a mixture of plant extracts obtained from at least two plants selected from the group consisting of: *Achillea millefolium; Aesuculus hippocastanum; Althaea officinalis; Avena sativa; Berberis vulgaris; Capsella Bursa Pastoris; Cochlearia officinalis; Conium maculatium; Ervum lens; Hamamelis virginiana; Hydrastis canadensis; Matricaria chamomilla; Nasturtium officinale; Phytolacca decendra; Pimpinella saxifraga; Populas alba; Populus tremuloides; Rhus toxicodendron; Sambucus nigra; Sanguinaria Canadensis; Scrophularia nodosa; Smilax medica; Tussilago farfara; Veronica officinalis*; and *Vincetoxicum officinale*. Also disclosed are compositions comprising the above compositions and a pharmaceutically acceptable carrier, diluents, or excipient. In addition, disclosed herein are methods of treating skin conditions by using the above compositions.

Thus, in a first non-limiting aspect, disclosed herein are complex herbal preparations containing a unique mixture of traditional commonly used multiple herbs. In some embodiments, the mixture comprises four herbal extract components. In certain embodiments, the disclosed preparations comprise plant extracts.

The term "plant extract" or "plant extracts" as used herein refers to a composition of extracted plant substances, including but not limited to: juices; macerations; concentrates; syrups; cold, heated, fluid and/or fermented extracts; powders; tablets; tinctures; herbal teas in the form of infusions or decoctions; poultices; lotions; creams; gels; ointments; salves; liniments; balms; oils; essential oils; suspensions; emulsions; compresses; dressings; fomentations; eyebaths; gargles; enemas; boluses; and other forms of extracted plant substances such as are known to those of ordinary skill in the arts of pharmacognosy, herbalism, and medicinal formulation. As used herein the term "plant extract" or "plant extracts" further contemplates the use of a solvent known to practitioners in this art for the purpose of extraction and or formulation, including but not limited to the use of one or more solvents such as water, an alcohol, a polyhydric alcohol, an ether, an ester, a carboxylic acid, an amide, a carbonate, supercritical fluid carbon dioxide, an ionic liquid, an alkane, a petroleum-derived oil, a plant oil, or another solvent, wherein the solvent employed is optionally part of a pH-adjusted medium. The term "plant extract" or "plant extracts" as used herein further contemplates that the extract may have been obtained by the use of one or more methods such as expression, absorption by steeping or otherwise, maceration, distillation, evaporation optionally with vacuum enhancement, freeze drying, and other methods known in the arts of substance isolation from natural sources.

In some embodiments, the disclosed preparations comprise a mixture of plant extracts from at least two plants selected from the group consisting of: *Achillea millefolium* (Yarrow); *Aesuculus hippocastanum* (Horsechestnut); *Althaea officinalis* (Althea mallow, or Marsh Mallow); *Avena sativa* (Oat); *Berberis vulgaris* (Barberry shrub); *Capsella Bursa Pastoris* (Shepherd's Purse); *Cochlearia officinalis* (Spoon Wort); *Conium maculatium* (Hemlock); *Ervum lens* (Lentil); *Hamamelis virginiana* (*Virginium Hamamelis*); *Hydrastis canadensis* (Orange Root); *Matricaria chamomilla* (Chamomil); *Nasturtium officinale* (Watercress); *Phytolacca decendra* (Poke Root); *Pimpinella saxifraga* (Pimpernal); *Populas alba* (White poplar); *Populus tremuloides* (Trembling poplar; Quaking Aspen, Trembling Aspen, Quakies); *Rhus toxicodendron* (Ivy); *Sambucus nigra* (Elderberry); *Sanguinaria Canadensis* (Canadian Blood root); *Scrophularia nodosa* (Figwort); *Smilax medica* (Sarsaparrilla); *Tussilago farfara* (Coltsfoot); *Veronica officinalis* (Speedwell); and *Vincetoxicum officinale* (Swallow Wort).

In some embodiments the herbal preparations disclosed herein comprise at least one herbal extract in the following amount (w/w):

*Achillea millefolium* from about 0.01% to about 20%;
*Aesuculus hippocastanum* from about 0.01% to about 20%;
*Althaea officinalis* from about 0.01% to about 20%;
*Avena sativa* from about 0.01% to about 25%;
*Berberis vulgaris* from about 0.01% to about 20%;
*Capsella Bursa Pastoris* from about 0.01% to about 20%;
*Cochlearia officinalis* from about 0.01% to about 20%;
*Conium maculatium* from about 0.01% to about 35%;
*Ervum lens* from about 0.01% to about 20%;
*Hamamelis virginiana* from about 0.01% to about 25%;
*Hydrastis canadensis* from about 0.01% to about 20%;
*Matricaria chamomilla* from about 0.01% to about 20%;
*Nasturtium officinale* from about 0.01% to about 15%;
*Phytolacca decendra* from about 0.01% to about 20%;
*Pimpinella saxifraga* from about 0.01% to about 20%;
*Populas alba* from about 0.01% to about 20%;
*Populus tremuloides* from about 0.01% to about 20%;
*Rhus toxicodendron* from about 0.01% to about 25%;
*Sambucus nigra* from about 0.01% to about 20;
*Sanguinaria Canadensis* from about 0.01% to about 20%;
*Scrophularia nodosa* from about 0.01% to about 20%;
*Smilax medica* from about 0.01% to about 20%;
*Tussilago farfara* from about 0.01% to about 15%;
*Veronica officinalis* from about 0.010% to about 15%; and
*Vincetoxicum officinale* from about 0.01% to about 15%.

Throughout the present disclosure the term "about" a certain value means that a range of value±20%, such as (but not limited to) a range of value±10%, is contemplated. Thus, for example, having about 20% w/w of an ingredient includes the ingredient being present between 16% and 24%, such as (but not limited to) between 18% and 22%.

In some embodiments the herbal preparations disclosed herein comprise *Achillea millefolium* from about 1% to about 15%; or from about 1% to about 10%; or from about 1% to about 8%; or from about 1.5% to about 7%; or from about 2% to about 6%. In some embodiments the herbal preparations disclosed herein comprise *Achillea millefolium* in about 2.5%, while in other embodiments comprise about 5%.

In some embodiments the herbal preparations disclosed herein comprise *Aesuculus hippocastanum* from about 1% to about 15%; or from about 1% to about 10%; or from about 1% to about 8%; or from about 1.5% to about 7%; or from about 2% to about 6%. In some embodiments the herbal preparations disclosed herein comprise *Aesuculus hippocastanum* in about 2.4%, while in other embodiments comprise about 5%.

In some embodiments the herbal preparations disclosed herein comprise *Althea officinalis* from about 1% to about 15%; or from about 1% to about 10%; or from about 1% to about 8%; or from about 1.5% to about 7%; or from about 1.5% to about 5%. In some embodiments the herbal preparations disclosed herein comprise *Althaea officinalis* in about 2.0%, while in other embodiments comprise about 4%.

In some embodiments the herbal preparations disclosed herein comprise *Avena sativa* from about 1% to about 25%; or from about 3% to about 20%; or from about 5% to about 17%; or from about 5% to about 15%. In some embodiments the herbal preparations disclosed herein comprise *Avena sativa* in about 6.8%, while in other embodiments comprise about 14%.

In some embodiments the herbal preparations disclosed herein comprise *Berberis vulgaris* from about 1% to about 17%; or from about 1% to about 15%; or from about 3% to about 12%; or from about 3% to about 10%. In some embodiments the herbal preparations disclosed herein comprise *Berberis vulgaris* in about 4.1%, while in other embodiments comprise about 8%.

In some embodiments the herbal preparations disclosed herein comprise *Capsella Bursa Pastoris* from about 1% to about 17%; or from about 1% to about 15%; or from about 1.5% to about 12%; or from about 1.5% to about 10%. In some embodiments the herbal preparations disclosed herein comprise *Capsella Bursa Pastoris* in about 2.2%, while in other embodiments comprise about 8%.

In some embodiments the herbal preparations disclosed herein comprise *Cochlearia officinalis* from about 1% to about 17%; or from about 3% to about 15%; or from about 3% to about 12%; or from about 4% to about 10%. In some embodiments the herbal preparations disclosed herein comprise *Cochlearia officinalis* in about 5.1%, while in other embodiments comprise about 10%.

In some embodiments the herbal preparations disclosed herein comprise *Conium maculatium* from about 1% to about 30%; or from about 1% to about 25%; or or from about 3.5% to about 23%. In some embodiments the herbal preparations disclosed herein comprise *Conium maculatium* in about 4%, in other embodiments comprise about 12.1%, while in yet other embodiments comprise about 21%.

In some embodiments the herbal preparations disclosed herein comprise *Ervum lens* from about 1% to about 17%; or from about 1% to about 15%; or from about 3% to about 12%; or from about 3% to about 10%. In some embodiments the herbal preparations disclosed herein comprise *Ervum lens* in about 3.7%, while in other embodiments comprise about 8%.

In some embodiments the herbal preparations disclosed herein comprise *Hamamelis virginiana* from about 1% to about 25%; or from about 3% to about 20%; or from about 5% to about 17%; or from about 5% to about 15%. In some embodiments the herbal preparations disclosed herein comprise *Hamamelis virginiana* in about 8.9%, while in other embodiments comprise about 13%.

In some embodiments the herbal preparations disclosed herein comprise *Hydrastis canadensis* from about 1% to about 17%; or from about 3% to about 15%; or from about 3% to about 12%; or from about 3.5% to about 10%. In some embodiments the herbal preparations disclosed herein comprise *Hydrastis canadensis* in about 5%, in other embodiments comprise about 6.0%, while in yet other embodiments comprise about 8%.

In some embodiments the herbal preparations disclosed herein comprise *Matricaria chamomilla* from about 1% to about 17%; or from about 1% to about 15%; or from about 1.5% to about 12%; or from about 1.5% to about 10%. In some embodiments the herbal preparations disclosed herein comprise *Matricaria chamomilla* in about 2.2%, while in other embodiments comprise about 8%.

In some embodiments the herbal preparations disclosed herein comprise *Nasturtium officinale* from about 0.01% to about 12%; or from about 0.01% to about 10%; or from about 0.1% to about 8%; or from about 0.1% to about 5%. In some embodiments the herbal preparations disclosed herein comprise *Nasturtium officinale* in about 0.9%, while in other embodiments comprise about 2%.

In some embodiments the herbal preparations disclosed herein comprise *Phytolacca decendra* from about 1% to about 17%; or from about 3% to about 15%; or from about 3% to about 12%; or from about 3.5% to about 10%. In some embodiments the herbal preparations disclosed herein comprise *Phytolacca decendra* in about 4%, in other embodiments comprise about 5.8%, while in yet other embodiments comprise about 8%.

In some embodiments the herbal preparations disclosed herein comprise *Pimpinella saxifraga* from about 0.01% to about 12%; or from about 0.01% to about 10%; or from about 0.1% to about 8%; or from about 0.5% to about 5%. In some embodiments the herbal preparations disclosed herein comprise *Pimpinella saxifraga* in about 1.1%, while in other embodiments comprise about 2%.

In some embodiments the herbal preparations disclosed herein comprise *Populas alba* from about 1% to about 17%; or from about 3% to about 15%; or from about 3% to about 12%; or from about 4% to about 10%. In some embodiments the herbal preparations disclosed herein comprise *Populas alba* in about 4.9%, while in other embodiments comprise about 10%.

In some embodiments the herbal preparations disclosed herein comprise *Populus tremuloides* from about 1% to about 17%; or from about 3% to about 15%; or from about 3% to about 12%; or from about 4% to about 10%. In some embodiments the herbal preparations disclosed herein comprise *Populus tremuloides* in about 4.8%, while in other embodiments comprise about 10%.

In some embodiments the herbal preparations disclosed herein comprise *Rhus toxicodendron* from about 1% to about 25%; or from about 3% to about 20%; or from about 5% to about 20%; or from about 7% to about 20%. In some embodiments the herbal preparations disclosed herein comprise *Rhus toxicodendron* in about 8.3%, while in other embodiments comprise about 17%.

In some embodiments the herbal preparations disclosed herein comprise *Sambucus nigra* from about 1% to about 15%; or from about 1% to about 10%; or from about 1% to about 8%; or from about 1.5% to about 7%; or from about 1.5% to about 6%. In some embodiments the herbal preparations disclosed herein comprise *Sambucus nigra* in about 1.9%, while in other embodiments comprise about 4%.

In some embodiments the herbal preparations disclosed herein comprise *Sanguinaria Canadensis* from about 1% to about 17%; or from about 3% to about 15%; or from about 3% to about 12%; or from about 4% to about 10%. In some embodiments the herbal preparations disclosed herein comprise *Sanguinaria Canadensis* in about 4.5%, while in other embodiments comprise about 9%.

In some embodiments the herbal preparations disclosed herein comprise *Scrophularia nodosa* from about 1% to about 17%; or from about 3% to about 15%; or from about 3% to about 12%; or from about 4% to about 10%. In some embodiments the herbal preparations disclosed herein comprise *Scrophularia nodosa* in about 4.0%, while in other embodiments comprise about 8%.

In some embodiments the herbal preparations disclosed herein comprise *Smilax medica* from about 1% to about 15%; or from about 1% to about 10%; or from about 1% to about 8%; or from about 1.5% to about 7%; or from about 2% to about 6.5%. In some embodiments the herbal preparations disclosed herein comprise *Smilax medica* in about 3.1%, while in other embodiments, comprise about 6%.

In some embodiments the herbal preparations disclosed herein comprise *Tussilago farfara* from about 0.01% to about 12%; or from about 0.01% to about 10%; or from about 0.1% to about 8%; or from about 0.1% to about 5%. In some embodiments the herbal preparations disclosed herein comprise *Tussilago farfara* in about 0.9%, while in other embodiments comprise about 2%.

In some embodiments the herbal preparations disclosed herein comprise *Veronica officinalis* from about 0.01% to about 12%; or from about 0.01% to about 10%; or from about 0.1% to about 8%; or from about 0.1% to about 5%.

In some embodiments the herbal preparations disclosed herein comprise *Veronica officinalis* in about 0.8%, while in other embodiments comprise about 2%.

In some embodiments the herbal preparations disclosed herein comprise *Vincetoxicum officinale* from about 0.01% to about 12%; or from about 0.01% to about 10%; or from about 0.1% to about 8%; or from about 0.1% to about 5%. In some embodiments the herbal preparations disclosed herein comprise *Vincetoxicum officinale* in about 0.9%, while in other embodiments comprise about 2%.

In one embodiment, the herbal preparation disclosed herein comprises Mixture I. Mixture I comprises plant extracts obtained from the following plants: *Althaea officinalis; Ervum lens; Populas alba; Populus tremuloides; Conium maculatium; Sambucus nigra; Hamamelis virginiana;* and *Phytolacca decendra.*

In another embodiment, the herbal preparation disclosed herein comprises Mixture II. Mixture II comprises plant extracts obtained from the following plants: *Conium maculatium; Phytolacca decendra; Pimpinella saxifraga; Rhus toxicodendron;* and *Vincetoxicum officinale.*

In yet another embodiment, the herbal preparation disclosed herein comprises Mixture III. Mixture III comprises plant extracts obtained from the following plants: *Avena sativa; Aesuculus hippocastanum; Capsella Bursa Pastoris; Hamamelis virginiana; Hydrastis canadensis; Achillea millefolium;* and *Sanguinaria Canadensis.*

In still another embodiment, the herbal preparation disclosed herein comprises Mixture IV. Mixture IV comprises plant extracts obtained from the following plants: *Berberis vulgaris; Matricaria chamomilla; Cochlearia officinalis; Hydrastis canadensis; Nasturtium officinale; Scrophularia nodosa; Smilax medica; Tussilago farfara;* and *Veronica officinalis.*

In one embodiment, the herbal preparation disclosed herein comprises Mixture V. Mixture V comprises plant extracts obtained from the following plants: *Berberis vulgaris; Cochlearia officinalis; Conium maculatium; Hydrastis canadensis; Matricaria chamomilla; Nasturtium officinale; Phytolacca decendra; Pimpinella saxifraga; Rhus toxicodendron; Scrophularia nodosa; Smilax medica; Tussilago farfara; Veronica officinalis;* and *Vincetoxicum officinale.*

In one embodiment, the herbal preparation disclosed herein comprises Mixture VI. Mixture VI comprises plant extracts obtained from the following plants: *Achillea millefolium; Aesuculus hippocastanum; Althaea officinalis; Avena sativa; Conium maculatium; Ervum lens; Hamamelis virginiana; Hydrastis canadensis; Phytolacca decendra; Populas alba; Populus tremuloides; Sambucus nigra;* and *Sanguinaria Canadensis.*

In some embodiments, the herbal preparation disclosed herein comprises a combination of Mixture I and Mixture II. In another embodiment, the herbal preparation disclosed herein comprises a combination of Mixture I and Mixture III. In another embodiment, the herbal preparation disclosed herein comprises a combination of Mixture I and Mixture IV.

In some embodiments, the herbal preparation disclosed herein comprises a combination of Mixture II and Mixture III. In another embodiment, the herbal preparation disclosed herein comprises a combination of Mixture II and Mixture IV.

In some embodiments, the herbal preparation disclosed herein comprises a combination of Mixture III and Mixture IV.

In some embodiments, the herbal preparation disclosed herein comprises a combination of Mixture I, Mixture II and Mixture III. In another embodiment, the herbal preparation disclosed herein comprises a combination of Mixture I, Mixture II and Mixture IV. In another embodiment, the herbal preparation disclosed herein comprises a combination of Mixture I, Mixture III and Mixture IV. In another embodiment, the herbal preparation disclosed herein comprises a combination of Mixture II, Mixture III and Mixture IV.

In another embodiment, the herbal preparation disclosed herein comprises a combination of Mixture I, Mixture II, Mixture Ill and Mixture IV.

In some embodiments, the herbal preparation disclosed herein comprises a combination of Mixture V and Mixture VI.

In some embodiments the herbal preparations disclosed herein comprise at least two herbal extracts each of which is selected from the following list and each is present in the following amount (w/w): *Achillea millefolium* from about 0.01% to about 20%; *Aesuculus hippocastanum* from about 0.01% to about 20%; *Althaea officinalis* from about 0.01% to about 20%; *Avena sativa* from about 0.01% to about 25%; *Berberis vulgaris* from about 0.01% to about 20%; *Capsella Bursa Pastoris* from about 0.01% to about 20%; *Cochlearia officinalis* from about 0.01% to about 20%; *Conium maculatium* from about 0.01% to about 35%; *Ervum lens* from about 0.01% to about 20%; *Hamamelis virginiana* from about 0.01% to about 25%; *Hydrastis canadensis* from about 0.01% to about 20%; *Matricaria chamomilla* from about 0.01% to about 20%; *Nasturtium officinale* from about 0.01% to about 15%; *Phytolacca decendra* from about 0.01% to about 20%; *Pimpinella saxifraga* from about 0.01% to about 20%; *Populas alba* from about 0.01% to about 20%; *Populus tremuloides* from about 0.01% to about 20%; *Rhus toxicodendron* from about 0.01% to about 25%; *Sambucus nigra* from about 0.01% to about 20; *Sanguinaria Canadensis* from about 0.01% to about 20%; *Scrophularia nodosa* from about 0.01% to about 20%; *Smilax medica* from about 0.01% to about 20%; *Tussilago farfara* from about 0.01% to about 15%; *Veronica officinalis* from about 0.01% to about 15%; and *Vincetoxicum officinale* from about 0.01% to about 15%.

In one embodiment, the herbal preparation disclosed herein comprises at least one plant extract from the Group I plant extracts and at least one plant extract from the Group II plant extracts, where the at least one Group I plant extract and the at least one Group II plant extract are different.

In one embodiment, the herbal preparation disclosed herein comprises at least one plant extract from the Group I plant extracts and at least one plant extract from the Group III plant extracts, where the at least one Group I plant extract and the at least one Group Ill plant extract are different.

In one embodiment, the herbal preparation disclosed herein comprises at least one plant extract from the Group I plant extracts and at least one plant extract from the Group IV plant extracts, where the at least one Group I plant extract and the at least one Group IV plant extract are different.

In one embodiment, the herbal preparation disclosed herein comprises at least one plant extract from the Group II plant extracts and at least one plant extract from the Group III plant extracts, where the at least one Group II plant extract and the at least one Group III plant extract are different.

In one embodiment, the herbal preparation disclosed herein comprises at least one plant extract from the Group II plant extracts and at least one plant extract from the Group IV plant extracts, where the at least one Group II plant extract and the at least one Group IV plant extract are different.

In one embodiment, the herbal preparation disclosed herein comprises at least one plant extract from the Group III plant extracts and at least one plant extract from the Group IV plant extracts, where the at least one Group III plant extract and the at least one Group IV plant extract are different.

In one embodiment, the herbal preparation disclosed herein comprises at least one plant extract from the Group I plant extracts, at least one plant extract from the Group II plant extracts, and at least one plant extract from the Group Ill plant extracts, where the at least one Group I plant extract, the at least one Group II plant extract, and the at least one Group Ill plant extract are different.

In one embodiment, the herbal preparation disclosed herein comprises at least one plant extract from the Group I plant extracts, at least one plant extract from the Group II plant extracts, and at least one plant extract from the Group IV plant extracts, where the at least one Group I plant extract, the at least one Group II plant extract, and the at least one Group IV plant extract are different.

In one embodiment, the herbal preparation disclosed herein comprises at least one plant extract from the Group I plant extracts, at least one plant extract from the Group III plant extracts, and at least one plant extract from the Group IV plant extracts, where the at least one Group I plant extract, the at least one Group Ill plant extract, and the at least one Group IV plant extract are different.

In one embodiment, the herbal preparation disclosed herein comprises at least one plant extract from the Group II plant extracts, at least one plant extract from the Group Ill plant extracts, and at least one plant extract from the Group IV plant extracts, where the at least one Group II plant extract, the at least one Group Ill plant extract, and the at least one Group IV plant extract are different.

Group I comprises a plant extract obtained from a plant selected from the group consisting of: *Althaea officinalis; Ervum lens; Populas alba; Populus tremuloides; Conium maculatium; Sambucus nigra; Hamamelis virginiana*; and *Phytolacca decendra*.

Group II comprises a plant extract obtained from a plant selected from the group consisting of: *Conium maculatium; Phytolacca decendra; Pimpinella saxifraga; Rhus toxicodendron*; and *Vincetoxicum officinale*.

Group Ill comprises a plant extract obtained from a plant selected from the group consisting of: *Avena sativa; Aesuculus hippocastanum; Capsella Bursa Pastoris; Hamamelis virginiana; Hydrastis canadensis; Achillea millefolium*; and *Sanguinaria Canadensis*.

Group IV comprises a plant extract obtained from a plant selected from the group consisting of: *Berberis vulgaris; Matricaria chamomilla; Cochlearia officinalis; Hydrastis canadensis; Nasturtium officinale; Scrophularia nodosa; Smilax medica; Tussilago farfara*; and *Veronica officinalis*.

Thus, embodiments of the herbal extracts disclosed herein include the mixtures numbered below in Table 1, comprising at least two components, where the components are listed in Table 1.

TABLE 1

| No. | Component 1 | Component 2 |
|---|---|---|
| 1 | *Achillea millefolium* from about 0.01% to about 20% | *Aesuculus hippocastanum* from about 0.01% to about 20% |
| 2 | *Achillea millefolium* from about 0.01% to about 20% | *Althaea officinalis* from about 0.01% to about 20% |
| 3 | *Achillea millefolium* from about 0.01% to about 20% | *Avena sativa* from about 0.01% to about 25% |
| 4 | *Achillea millefolium* from about 0.01% to about 20% | *Berberis vulgaris* from about 0.01% to about 20% |
| 5 | *Achillea millefolium* from about 0.01% to about 20% | *Cochlearia officinalis* from about 0.01% to about 20% |
| 6 | *Achillea millefolium* from about 0.01% to about 20% | *Conium maculatium* from about 0.01% to about 35% |
| 7 | *Achillea millefolium* from about 0.01% to about 20% | *Ervum lens* from about 0.01% to about 20% |
| 8 | *Achillea millefolium* from about 0.01% to about 20% | *Hamamelis virginiana* from about 0.01% to about 25% |
| 9 | *Achillea millefolium* from about 0.01% to about 20% | *Hydrastis canadensis* from about 0.01% to about 20% |
| 10 | *Achillea millefolium* from about 0.01% to about 20% | *Copsella Bursa Pastoris* from about 0.01% to about 20% |
| 11 | *Achillea millefolium* from about 0.01% to about 20% | *Matricaria chamomilla* from about 0.01% to about 20% |
| 12 | *Achillea millefolium* from about 0.01% to about 20% | *Nasturtium officinale* from about 0.01% to about 15% |
| 13 | *Achillea millefolium* from about 0.01% to about 20% | *Phytolacca decendra* from about 0.01% to about 20% |
| 14 | *Achillea millefolium* from about 0.01% to about 20% | *Pimpinella saxifraga* from about 0.01% to about 20% |
| 15 | *Achillea millefolium* from about 0.01% to about 20% | *Populas alba* from about 0.01% to about 20% |
| 16 | *Achillea millefolium* from about 0.01% to about 20% | *Populus tremuloides* from about 0.01% to about 20% |
| 17 | *Achillea millefolium* from about 0.01% to about 20% | *Rhus toxicodendron* from about 0.01% to about 25% |
| 18 | *Achillea millefolium* from about 0.01% to about 20% | *Sambucus nigra* from about 0.01% to about 20% |
| 19 | *Achillea millefolium* from about 0.01% to about 20% | *Sanguinaria Canadensis* from about 0.01% to about 20% |
| 20 | *Achillea millefolium* from about 0.01% to about 20% | *Scrophularia nodosa* from about 0.01% to about 20% |
| 21 | *Achillea millefolium* from about 0.01% to about 20% | *Smilax medica* from about 0.01% to about 20% |
| 22 | *Achillea millefolium* from about 0.01% to about 20% | *Tussilago farfara* from about 0.01% to about 15% |
| 23 | *Achillea millefolium* from about 0.01% to about 20% | *Veronica officinalis* from about 0.01% to about 15% |
| 24 | *Achillea millefolium* from about 0.01% to about 20% | *Vincetoxicum officinale* from about 0.01% to about 15% |
| 25 | *Aesuculus hippocastanum* from about 0.01% to about 20% | *Althaea officinalis* from about 0.01% to about 20% |
| 26 | *Aesuculus hippocastanum* from about 0.01% to about 20% | *Avena sativa* from about 0.01% to about 25% |
| 27 | *Aesuculus hippocastanum* from about 0.01% to about 20% | *Berberis vulgaris* from about 0.01% to about 20% |
| 28 | *Aesuculus hippocastanum* from about 0.01% to about 20% | *Cochlearia officinalis* from about 0.01% to about 20% |
| 29 | *Aesuculus hippocastanum* from about 0.01% to about 20% | *Conium maculatium* from about 0.01% to about 35% |
| 30 | *Aesuculus hippocastanum* from about 0.01% to about 20% | *Ervum lens* from about 0.01% to about 20% |
| 31 | *Aesuculus hippocastanum* from about 0.01% to about 20% | *Hamamelis virginiana* from about 0.01% to about 25% |
| 32 | *Aesuculus hippocastanum* from about 0.01% to about 20% | *Hydrastis canadensis* from about 0.01% to about 20% |
| 33 | *Aesuculus hippocastanum* from about 0.01% to about 20% | *Capsella Bursa Pastoris* from about 0.01% to about 20% |
| 34 | *Aesuculus hippocastanum* from about 0.01% to about 20% | *Matricaria chamomilla* from about 0.01% to about 20% |
| 35 | *Aesuculus hippocastanum* from about 0.01% to about 20% | *Nasturtium officinale* from about 0.01% to about 15% |
| 36 | *Aesuculus hippocastanum* from about 0.01% to about 20% | *Phytolacca decendra* from about 0.01% to about 20% |
| 37 | *Aesuculus hippocastanum* from about 0.01% to about 20% | *Pimpinella saxifraga* from about 0.01% to about 20% |
| 38 | *Aesuculus hippocastanum* from about 0.01% to about 20% | *Populas alba* from about 0.01% to about 20% |
| 39 | *Aesuculus hippocastanum* from about 0.01% to about 20% | *Populus tremuloides* from about 0.01% to about 20% |

TABLE 1-continued

| No. | Component 1 | Component 2 |
|---|---|---|
| 40 | *Aesuculus hippocastanum* from about 0.01% to about 20% | *Rhus toxicodendron* from about 0.01% to about 25% |
| 41 | *Aesuculus hippocastanum* from about 0.01% to about 20% | *Sambucus nigra* from about 0.01% to about 20% |
| 42 | *Aesuculus hippocastanum* from about 0.01% to about 20% | *Sanguinaria Canadensis* from about 0.01% to about 20% |
| 43 | *Aesuculus hippocastanum* from about 0.01% to about 20% | *Scrophularia nodosa* from about 0.01% to about 20% |
| 44 | *Aesuculus hippocastanum* from about 0.01% to about 20% | *Smilax medica* from about 0.01% to about 20% |
| 45 | *Aesuculus hippocastanum* from about 0.01% to about 20% | *Tussilago farfara* from about 0.01% to about 15% |
| 46 | Aesuculus hippocastanum from about 0.01% to about 20% | *Veronica officinalis* from about 0.01% to about 15% |
| 47 | Aesuculus hippocastanum from about 0.01% to about 20% | *Vincetoxicum officinale* from about 0.01% to about 15% |
| 48 | *Althaea officinalis* from about 0.01% to about 20% | *Avena sativa* from about 0.01% to about 25% |
| 49 | *Althaea officinalis* from about 0.01% to about 20% | *Berberis vulgaris* from about 0.01% to about 20% |
| 50 | *Althaea officinalis* from about 0.01% to about 20% | *Cochlearia officinalis* from about 0.01% to about 20% |
| 51 | *Althaea officinalis* from about 0.01% to about 20% | *Conium maculatium* from about 0.01% to about 35% |
| 52 | *Althaea officinalis* from about 0.01% to about 20% | *Ervum lens* from about 0.01% to about 20% |
| 53 | *Althaea officinalis* from about 0.01% to about 20% | *Hamamelis virginiana* from about 0.01% to about 25% |
| 54 | *Althaea officinalis* from about 0.01% to about 20% | *Hydrastis canadensis* from about 0.01% to about 20% |
| 55 | *Althaea officinalis* from about 0.01% to about 20% | *Capsella Bursa Pastoris* from about 0.01% to about 20% |
| 56 | *Althaea officinalis* from about 0.01% to about 20% | *Matricaria chamomilla* from about 0.01% to about 20% |
| 57 | *Althaea officinalis* from about 0.01% to about 20% | *Nasturtium officinale* from about 0.01% to about 15% |
| 58 | *Althaea officinalis* from about 0.01% to about 20% | *Phytolacca decendra* from about 0.01% to about 20% |
| 59 | *Althaea officinalis* from about 0.01% to about 20% | *Pimpinella saxifraga* from about 0.01% to about 20% |
| 60 | *Althaea officinalis* from about 0.01% to about 20% | *Populas alba* from about 0.01% to about 20% |
| 61 | *Althaea officinalis* from about 0.01% to about 20% | *Populus tremuloides* from about 0.01% to about 20% |
| 62 | *Althaea officinalis* from about 0.01% to about 20% | *Rhus toxicodendron* from about 0.01% to about 25% |
| 63 | *Althaea officinalis* from about 0.01% to about 20% | *Sambucus nigra* from about 0.01% to about 20% |
| 64 | *Althaea officinalis* from about 0.01% to about 20% | *Sanguinaria Canadensis* from about 0.01% to about 20% |
| 65 | *Althaea officinalis* from about 0.01% to about 20% | *Scrophularia nodosa* from about 0.01% to about 20% |
| 66 | *Althaea officinalis* from about 0.01% to about 20% | *Smilax medica* from about 0.01% to about 20% |
| 67 | *Althaea officinalis* from about 0.01% to about 20% | *Tussilago farfara* from about 0.01% to about 15% |
| 68 | *Althaea officinalis* from about 0.01% to about 20% | *Veronica officinalis* from about 0.01% to about 15% |
| 69 | *Althaea officinalis* from about 0.01% to about 20% | *Vincetoxicum officinale* from about 0.01% to about 15% |
| 70 | *Avena sativa* from about 0.01% to about 25% | *Berberis vulgaris* from about 0.01% to about 20% |
| 71 | *Avena sativa* from about 0.01% to about 25% | *Cochlearia officinalis* from about 0.01% to about 20% |
| 72 | *Avena sativa* from about 0.01% to about 25% | *Conium maculatium* from about 0.01% to about 35% |
| 73 | *Avena sativa* from about 0.01% to about 25% | *Ervum lens* from about 0.01% to about 20% |
| 74 | *Avena sativa* from about 0.01% to about 25% | *Hamamelis virginiana* from about 0.01% to about 25% |
| 75 | *Avena sativa* from about 0.01% to about 25% | *Hydrastis canadensis* from about 0.01% to about 20% |
| 76 | *Avena sativa* from about 0.01% to about 25% | *Capsella Bursa Pastoris* from about 0.01% to about 20% |
| 77 | *Avena sativa* from about 0.01% to about 25% | *Matricaria chamomilla* from about 0.01% to about 20% |
| 78 | *Avena sativa* from about 0.01% to about 25% | *Nasturtium officinale* from about 0.01% to about 15% |

TABLE 1-continued

| No. | Component 1 | Component 2 |
|---|---|---|
| 79 | *Avena sativa* from about 0.01% to about 25% | *Phytolacca decendra* from about 0.01% to about 20% |
| 80 | *Avena sativa* from about 0.01% to about 25% | *Pimpinella saxifraga* from about 0.01% to about 20% |
| 81 | *Avena sativa* from about 0.01% to about 25% | *Populas alba* from about 0.01% to about 20% |
| 82 | *Avena sativa* from about 0.01% to about 25% | *Populus tremuloides* from about 0.01% to about 20% |
| 83 | *Avena sativa* from about 0.01% to about 25% | *Rhus toxicodendron* from about 0.01% to about 25% |
| 84 | *Avena sativa* from about 0.01% to about 25% | *Sambucus nigra* from about 0.01% to about 20% |
| 85 | *Avena sativa* from about 0.01% to about 25% | *Sanguinaria Canadensis* from about 0.01% to about 20% |
| 86 | *Avena sativa* from about 0.01% to about 25% | *Scrophularia nodosa* from about 0.01% to about 20% |
| 87 | *Avena sativa* from about 0.01% to about 25% | *Smilax medica* from about 0.01% to about 20% |
| 88 | *Avena sativa* from about 0.01% to about 25% | *Tussilago farfara* from about 0.01% to about 15% |
| 89 | *Avena sativa* from about 0.01% to about 25% | *Veronica officinalis* from about 0.01% to about 15% |
| 90 | *Avena sativa* from about 0.01% to about 25% | *Vincetoxicum officinale* from about 0.01% to about 15% |
| 91 | *Berberis vulgaris* from about 0.01% to about 20% | *Cochlearia officinalis* from about 0.01% to about 20% |
| 92 | *Berberis vulgaris* from about 0.01% to about 20% | *Conium maculatium* from about 0.01% to about 35% |
| 93 | *Berberis vulgaris* from about 0.01% to about 20% | *Ervum lens* from about 0.01% to about 20% |
| 94 | *Berberis vulgaris* from about 0.01% to about 20% | *Hamamelis virginiana* from about 0.01% to about 25% |
| 95 | *Berberis vulgaris* from about 0.01% to about 20% | *Hydrastis canadensis* from about 0.01% to about 20% |
| 96 | *Berberis vulgaris* from about 0.01% to about 20% | *Copsella Bursa Pastoris* from about 0.01% to about 20% |
| 97 | *Berberis vulgaris* from about 0.01% to about 20% | *Matricaria chamomilla* from about 0.01% to about 20% |
| 98 | *Berberis vulgaris* from about 0.01% to about 20% | *Nasturtium officinale* from about 0.01% to about 15% |
| 99 | *Berberis vulgaris* from about 0.01% to about 20% | *Phytolacca decendra* from about 0.01% to about 20% |
| 100 | *Berberis vulgaris* from about 0.01% to about 20% | *Pimpinella saxifraga* from about 0.01% to about 20% |
| 101 | *Berberis vulgaris* from about 0.01% to about 20% | *Populas alba* from about 0.01% to about 20% |
| 102 | *Berberis vulgaris* from about 0.01% to about 20% | *Populus tremuloides* from about 0.01% to about 20% |
| 103 | *Berberis vulgaris* from about 0.01% to about 20% | *Rhus toxicodendron* from about 0.01% to about 25% |
| 104 | *Berberis vulgaris* from about 0.01% to about 20% | *Sambucus nigra* from about 0.01% to about 20% |
| 105 | *Berberis vulgaris* from about 0.01% to about 20% | *Sanguinaria Canadensis* from about 0.01% to about 20% |
| 106 | *Berberis vulgaris* from about 0.01% to about 20% | *Scrophularia nodosa* from about 0.01% to about 20% |
| 107 | *Berberis vulgaris* from about 0.01% to about 20% | *Smilax medica* from about 0.01% to about 20% |
| 108 | *Berberis vulgaris* from about 0.01% to about 20% | *Tussilago farfara* from about 0.01% to about 15% |
| 109 | Berberis vulgaris from about 0.01% to about 20% | *Veronica officinalis* from about 0.01% to about 15% |
| 110 | *Berberis vulgaris* from about 0.01% to about 20% | *Vincetoxicum officinale* from about 0.01% to about 15% |
| 111 | *Cochlearia officinalis* from about 0.01% to about 20% | *Conium maculatium* from about 0.01% to about 35% |
| 112 | *Cochlearia officinalis* from about 0.01% to about 20% | *Ervum lens* from about 0.01% to about 20% |
| 113 | *Cochlearia officinalis* from about 0.01% to about 20% | *Hamamelis virginiana* from about 0.01% to about 25% |
| 114 | *Cochlearia officinalis* from about 0.01% to about 20% | *Hydrastis canadensis* from about 0.01% to about 20% |
| 115 | *Cochlearia officinalis* from about 0.01% to about 20% | *Capsella Bursa Pastoris* from about 0.01% to about 20% |
| 116 | *Cochlearia officinalis* from about 0.01% to about 20% | *Matricaria chamomilla* from about 0.01% to about 20% |
| 117 | *Cochlearia officinalis* from about 0.01% to about 20% | *Nasturtium officinale* from about 0.01% to about 15% |

TABLE 1-continued

| No. | Component 1 | Component 2 |
|---|---|---|
| 118 | *Cochlearia officinalis* from about 0.01% to about 20% | *Phytolacca decendra* from about 0.01% to about 20% |
| 119 | *Cochlearia officinalis* from about 0.01% to about 20% | *Pimpinella saxifraga* from about 0.01% to about 20% |
| 120 | *Cochlearia officinalis* from about 0.01% to about 20% | *Populas alba* from about 0.01% to about 20% |
| 121 | *Cochlearia officinalis* from about 0.01% to about 20% | *Populus tremuloides* from about 0.01% to about 20% |
| 122 | *Cochlearia officinalis* from about 0.01% to about 20% | *Rhus toxicodendron* from about 0.01% to about 25% |
| 123 | *Cochlearia officinalis* from about 0.01% to about 20% | *Sambucus nigra* from about 0.01% to about 20% |
| 124 | *Cochlearia officinalis* from about 0.01% to about 20% | *Sanguinaria Canadensis* from about 0.01% to about 20% |
| 125 | *Cochlearia officinalis* from about 0.01% to about 20% | *Scrophularia nodosa* from about 0.01% to about 20% |
| 126 | *Cochlearia officinalis* from about 0.01% to about 20% | *Smilax medica* from about 0.01% to about 20% |
| 127 | *Cochlearia officinalis* from about 0.01% to about 20% | *Tussilago farfara* from about 0.01% to about 15% |
| 128 | *Cochlearia officinalis* from about 0.01% to about 20% | *Veronica officinalis* from about 0.01% to about 15% |
| 129 | *Cochlearia officinalis* from about 0.01% to about 20% | *Vincetoxicum officinale* from about 0.01% to about 15% |
| 130 | *Conium maculatium* from about 0.01% to about 35% | *Ervum lens* from about 0.01% to about 20% |
| 131 | *Conium maculatium* from about 0.01% to about 35% | *Hamamelis virginiana* from about 0.01% to about 25% |
| 132 | *Conium maculatium* from about 0.01% to about 35% | *Hydrastis canadensis* from about 0.01% to about 20% |
| 133 | *Conium maculatium* from about 0.01% to about 35% | *Capsella Bursa Pastoris* from about 0.01% to about 20% |
| 134 | *Conium maculatium* from about 0.01% to about 35% | *Matricaria chamomilla* from about 0.01% to about 20% |
| 135 | *Conium maculatium* from about 0.01% to about 35% | *Nasturtium officinale* from about 0.01% to about 15% |
| 136 | *Conium maculatium* from about 0.01% to about 35% | *Phytolacca decendra* from about 0.01% to about 20% |
| 137 | *Conium maculatium* from about 0.01% to about 35% | *Pimpinella saxifraga* from about 0.01% to about 20% |
| 138 | *Conium maculatium* from about 0.01% to about 35% | *Populas alba* from about 0.01% to about 20% |
| 139 | *Conium maculatium* from about 0.01% to about 35% | *Populus tremuloides* from about 0.01% to about 20% |
| 140 | *Conium maculatium* from about 0.01% to about 35% | *Rhus toxicodendron* from about 0.01% to about 25% |
| 141 | *Conium maculatium* from about 0.01% to about 35% | *Sambucus nigra* from about 0.01% to about 20% |
| 142 | *Conium maculatium* from about 0.01% to about 35% | *Sanguinaria Canadensis* from about 0.01% to about 20% |
| 143 | *Conium maculatium* from about 0.01% to about 35% | *Scrophularia nodosa* from about 0.01% to about 20% |
| 144 | *Conium maculatium* from about 0.01% to about 35% | *Smilax medica* from about 0.01% to about 20% |
| 145 | *Conium maculatium* from about 0.01% to about 35% | *Tussilago farfara* from about 0.01% to about 15% |
| 146 | *Conium maculatium* from about 0.01% to about 35% | *Veronica officinalis* from about 0.01% to about 15% |
| 147 | *Conium maculatium* from about 0.01% to about 35% | *Vincetoxicum officinale* from about 0.01% to about 15% |
| 148 | *Ervum lens* from about 0.01% to about 20% | *Hamamelis virginiana* from about 0.01% to about 25% |
| 149 | *Ervum lens* from about 0.01% to about 20% | *Hydrastis canadensis* from about 0.01% to about 20% |
| 150 | *Ervum lens* from about 0.01% to about 20% | *Capsella Bursa Pastoris* from about 0.01% to about 20% |
| 151 | *Ervum lens* from about 0.01% to about 20% | *Matricaria chamomilla* from about 0.01% to about 20% |
| 152 | *Ervum lens* from about 0.01% to about 20% | *Nasturtium officinale* from about 0.01% to about 15% |
| 153 | *Ervum lens* from about 0.01% to about 20% | *Phytolacca decendra* from about 0.01% to about 20% |
| 154 | *Ervum lens* from about 0.01% to about 20% | *Pimpinella saxifraga* from about 0.01% to about 20% |
| 155 | *Ervum lens* from about 0.01% to about 20% | *Populas alba* from about 0.01% to about 20% |
| 156 | *Ervum lens* from about 0.01% to about 20% | *Populus tremuloides* from about 0.01% to about 20% |

TABLE 1-continued

| No. | Component 1 | Component 2 |
|---|---|---|
| 157 | *Ervum lens* from about 0.01% to about 20% | *Rhus toxicodendron* from about 0.01% to about 25% |
| 158 | *Ervum lens* from about 0.01% to about 20% | *Sambucus nigra* from about 0.01% to about 20% |
| 159 | *Ervum lens* from about 0.01% to about 20% | *Sanguinaria Canadensis* from about 0.01% to about 20% |
| 160 | *Ervum lens* from about 0.01% to about 20% | *Scrophularia nodosa* from about 0.01% to about 20% |
| 161 | *Ervum lens* from about 0.01% to about 20% | *Smilax medica* from about 0.01% to about 20% |
| 162 | *Ervum lens* from about 0.01% to about 20% | *Tussilago farfara* from about 0.01% to about 15% |
| 163 | *Ervum lens* from about 0.01% to about 20% | *Veronica officinalis* from about 0.01% to about 15% |
| 164 | *Ervum lens* from about 0.01% to about 20% | *Vincetoxicum officinale* from about 0.01% to about 15% |
| 165 | *Hamamelis virginiana* from about 0.01% to about 25% | *Hydrastis canadensis* from about 0.01% to about 20% |
| 166 | *Hamamelis virginiana* from about 0.01% to about 25% | *Capsella Bursa Pastoris* from about 0.01% to about 20% |
| 167 | *Hamamelis virginiana* from about 0.01% to about 25% | *Matricaria chamomilla* from about 0.01% to about 20% |
| 168 | *Hamamelis virginiana* from about 0.01% to about 25% | *Nasturtium officinale* from about 0.01% to about 15% |
| 169 | *Hamamelis virginiana* from about 0.01% to about 25% | *Phytolacca decendra* from about 0.01% to about 20% |
| 170 | *Hamamelis virginiana* from about 0.01% to about 25% | *Pimpinella saxifraga* from about 0.01% to about 20% |
| 171 | *Hamamelis virginiana* from about 0.01% to about 25% | *Populas alba* from about 0.01% to about 20% |
| 172 | *Hamamelis virginiana* from about 0.01% to about 25% | *Populus tremuloides* from about 0.01% to about 20% |
| 173 | *Hamamelis virginiana* from about 0.01% to about 25% | *Rhus toxicodendron* from about 0.01% to about 25% |
| 174 | *Hamamelis virginiana* from about 0.01% to about 25% | *Sambucus nigra* from about 0.01% to about 20% |
| 175 | *Hamamelis virginiana* from about 0.01% to about 25% | *Sanguinaria Canadensis* from about 0.01% to about 20% |
| 176 | *Hamamelis virginiana* from about 0.01% to about 25% | *Scrophularia nodosa* from about 0.01% to about 20% |
| 177 | *Hamamelis virginiana* from about 0.01% to about 25% | *Smilax medica* from about 0.01% to about 20% |
| 178 | *Hamamelis virginiana* from about 0.01% to about 25% | *Tussilago farfara* from about 0.01% to about 15% |
| 179 | *Hamamelis virginiana* from about 0.01% to about 25% | *Veronica officinalis* from about 0.01% to about 15% |
| 180 | *Hamamelis virginiana* from about 0.01% to about 25% | *Vincetoxicum officinale* from about 0.01% to about 15% |
| 181 | *Hydrastis canadensis* from about 0.01% to about 20% | *Capsella Bursa Pastoris* from about 0.01% to about 20% |
| 182 | *Hydrastis canadensis* from about 0.01% to about 20% | *Matricaria chamomilla* from about 0.01% to about 20% |
| 183 | *Hydrastis canadensis* from about 0.01% to about 20% | *Nasturtium officinale* from about 0.01% to about 15% |
| 184 | *Hydrastis canadensis* from about 0.01% to about 20% | *Phytolacca decendra* from about 0.01% to about 20% |
| 185 | *Hydrastis canadensis* from about 0.01% to about 20% | *Pimpinella saxifraga* from about 0.01% to about 20% |
| 186 | *Hydrastis canadensis* from about 0.01% to about 20% | *Populas alba* from about 0.01% to about 20% |
| 187 | *Hydrastis canadensis* from about 0.01% to about 20% | *Populus tremuloides* from about 0.01% to about 20% |
| 188 | *Hydrastis canadensis* from about 0.01% to about 20% | *Rhus toxicodendron* from about 0.01% to about 25% |
| 189 | *Hydrastis canadensis* from about 0.01% to about 20% | *Sambucus nigra* from about 0.01% to about 20% |
| 190 | *Hydrastis canadensis* from about 0.01% to about 20% | *Sanguinaria Canadensis* from about 0.01% to about 20% |
| 191 | *Hydrastis canadensis* from about 0.01% to about 20% | *Scrophularia nodosa* from about 0.01% to about 20% |
| 192 | *Hydrastis canadensis* from about 0.01% to about 20% | *Smilax medica* from about 0.01% to about 20% |
| 193 | *Hydrastis canadensis* from about 0.01% to about 20% | *Tussilago farfara* from about 0.01% to about 15% |
| 194 | *Hydrastis canadensis* from about 0.01% to about 20% | *Veronica officinalis* from about 0.01% to about 15% |
| 195 | *Hydrastis canadensis* from about 0.01% to about 20% | *Vincetoxicum officinale* from about 0.01% to about 15% |

TABLE 1-continued

| No. | Component 1 | Component 2 |
|---|---|---|
| 196 | *Capsella Bursa Pastoris* from about 0.01% to about 20% | *Matricaria chamomilla* from about 0.01% to about 20% |
| 197 | *Capsella Bursa Pastoris* from about 0.01% to about 20% | *Nasturtium officinale* from about 0.01% to about 15% |
| 198 | *Capsella Bursa Pastoris* from about 0.01% to about 20% | *Phytolacca decendra* from about 0.01% to about 20% |
| 199 | *Capsella Bursa Pastoris* from about 0.01% to about 20% | *Pimpinella saxifraga* from about 0.01% to about 20% |
| 200 | *Capsella Bursa Pastoris* from about 0.01% to about 20% | *Populas alba* from about 0.01% to about 20% |
| 201 | *Capsella Bursa Pastoris* from about 0.01% to about 20% | *Populus tremuloides* from about 0.01% to about 20% |
| 202 | *Capsella Bursa Pastoris* from about 0.01% to about 20% | *Rhus toxicodendron* from about 0.01% to about 25% |
| 203 | *Capsella Bursa Pastoris* from about 0.01% to about 20% | *Sambucus nigra* from about 0.01% to about 20% |
| 204 | *Capsella Bursa Pastoris* from about 0.01% to about 20% | *Sanguinaria Canadensis* from about 0.01% to about 20% |
| 205 | *Capsella Bursa Pastoris* from about 0.01% to about 20% | *Scrophularia nodosa* from about 0.01% to about 20% |
| 206 | *Capsella Bursa Pastoris* from about 0.01% to about 20% | *Smilax medica* from about 0.01% to about 20% |
| 207 | *Capsella Bursa Pastoris* from about 0.01% to about 20% | *Tussilago farfara* from about 0.01% to about 15% |
| 208 | *Capsella Bursa Pastoris* from about 0.01% to about 20% | *Veronica officinalis* from about 0.01% to about 15% |
| 209 | *Capsella Bursa Pastoris* from about 0.01% to about 20% | *Vincetoxicum officinale* from about 0.01% to about 15% |
| 210 | *Matricaria chamomilla* from about 0.01% to about 20% | *Nasturtium officinale* from about 0.01% to about 15% |
| 211 | *Matricaria chamomilla* from about 0.01% to about 20% | *Phytolacca decendra* from about 0.01% to about 20% |
| 212 | *Matricaria chamomilla* from about 0.01% to about 20% | *Pimpinella saxifraga* from about 0.01% to about 20% |
| 213 | *Matricaria chamomilla* from about 0.01% to about 20% | *Populas alba* from about 0.01% to about 20% |
| 214 | *Matricaria chamomilla* from about 0.01% to about 20% | *Populus tremuloides* from about 0.01% to about 20% |
| 215 | *Matricaria chamomilla* from about 0.01% to about 20% | *Rhus toxicodendron* from about 0.01% to about 25% |
| 216 | *Matricaria chamomilla* from about 0.01% to about 20% | *Sambucus nigra* from about 0.01% to about 20% |
| 217 | *Matricaria chamomilla* from about 0.01% to about 20% | *Sanguinaria Canadensis* from about 0.01% to about 20% |
| 218 | *Matricaria chamomilla* from about 0.01% to about 20% | *Scrophularia nodosa* from about 0.01% to about 20% |
| 219 | *Matricaria chamomilla* from about 0.01% to about 20% | *Smilax medica* from about 0.01% to about 20% |
| 220 | *Matricaria chamomilla* from about 0.01% to about 20% | *Tussilago farfara* from about 0.01% to about 15% |
| 221 | *Matricaria chamomilla* from about 0.01% to about 20% | *Veronica officinalis* from about 0.01% to about 15% |
| 222 | *Matricaria chamomilla* from about 0.01% to about 20% | *Vincetoxicum officinale* from about 0.01% to about 15% |
| 223 | *Nasturtium officinale* from about 0.01% to about 15% | *Phytolacca decendra* from about 0.01% to about 20% |
| 224 | *Nasturtium officinale* from about 0.01% to about 15% | *Pimpinella saxifraga* from about 0.01% to about 20% |
| 225 | *Nasturtium officinale* from about 0.01% to about 15% | *Populas alba* from about 0.01% to about 20% |
| 226 | *Nasturtium officinale* from about 0.01% to about 15% | *Populus tremuloides* from about 0.01% to about 20% |
| 227 | *Nasturtium officinale* from about 0.01% to about 15% | *Rhus toxicodendron* from about 0.01% to about 25% |
| 228 | *Nasturtium officinale* from about 0.01% to about 15% | *Sambucus nigra* from about 0.01% to about 20% |
| 229 | *Nasturtium officinale* from about 0.01% to about 15% | *Sanguinaria Canadensis* from about 0.01% to about 20% |
| 230 | *Nasturtium officinale* from about 0.01% to about 15% | *Scrophularia nodosa* from about 0.01% to about 20% |
| 231 | *Nasturtium officinale* from about 0.01% to about 15% | *Smilax medica* from about 0.01% to about 20% |
| 232 | *Nasturtium officinale* from about 0.01% to about 15% | *Tussilago farfara* from about 0.01% to about 15% |
| 233 | *Nasturtium officinale* from about 0.01% to about 15% | *Veronica officinalis* from about 0.01% to about 15% |
| 234 | *Nasturtium officinale* from about 0.01% to about 15% | *Vincetoxicum officinale* from about 0.01% to about 15% |

TABLE 1-continued

| No. | Component 1 | Component 2 |
|---|---|---|
| 235 | *Phytolacca decendra* from about 0.01% to about 20% | *Pimpinella saxifraga* from about 0.01% to about 20% |
| 236 | *Phytolacca decendra* from about 0.01% to about 20% | *Populas alba* from about 0.01% to about 20% |
| 237 | *Phytolacca decendra* from about 0.01% to about 20% | *Populus tremuloides* from about 0.01% to about 20% |
| 238 | *Phytolacca decendra* from about 0.01% to about 20% | *Rhus toxicodendron* from about 0.01% to about 25% |
| 239 | *Phytolacca decendra* from about 0.01% to about 20% | *Sambucus nigra* from about 0.01% to about 20% |
| 240 | *Phytolacca decendra* from about 0.01% to about 20% | *Sanguinaria Canadensis* from about 0.01% to about 20% |
| 241 | *Phytolacca decendra* from about 0.01% to about 20% | *Scrophularia nodosa* from about 0.01% to about 20% |
| 242 | *Phytolacca decendra* from about 0.01% to about 20% | *Smilax medica* from about 0.01% to about 20% |
| 243 | *Phytolacca decendra* from about 0.01% to about 20% | *Tussilago farfara* from about 0.01% to about 15% |
| 244 | *Phytolacca decendra* from about 0.01% to about 20% | *Veronica officinalis* from about 0.01% to about 15% |
| 245 | *Phytolacca decendra* from about 0.01% to about 20% | *Vincetoxicum officinale* from about 0.01% to about 15% |
| 246 | *Pimpinella saxifraga* from about 0.01% to about 20% | *Populas alba* from about 0.01% to about 20% |
| 247 | *Pimpinella saxifraga* from about 0.01% to about 20% | *Populus tremuloides* from about 0.01% to about 20% |
| 248 | *Pimpinella saxifraga* from about 0.01% to about 20% | *Rhus toxicodendron* from about 0.01% to about 25% |
| 249 | *Pimpinella saxifraga* from about 0.01% to about 20% | *Sambucus nigra* from about 0.01% to about 20% |
| 250 | *Pimpinella saxifraga* from about 0.01% to about 20% | *Sanguinaria Canadensis* from about 0.01% to about 20% |
| 251 | *Pimpinella saxifraga* from about 0.01% to about 20% | *Scrophularia nodosa* from about 0.01% to about 20% |
| 252 | *Pimpinella saxifraga* from about 0.01% to about 20% | *Smilax medica* from about 0.01% to about 20% |
| 253 | *Pimpinella saxifraga* from about 0.01% to about 20% | *Tussilago farfara* from about 0.01% to about 15% |
| 254 | *Pimpinella saxifraga* from about 0.01% to about 20% | *Veronica officinalis* from about 0.01% to about 15% |
| 255 | *Pimpinella saxifraga* from about 0.01% to about 20% | *Vincetoxicum officinale* from about 0.01% to about 15% |
| 256 | *Populas alba* from about 0.01% to about 20% | *Populus tremuloides* from about 0.01% to about 20% |
| 257 | *Populas alba* from about 0.01% to about 20% | *Rhus toxicodendron* from about 0.01% to about 25% |
| 258 | *Populas alba* from about 0.01% to about 20% | *Sambucus nigra* from about 0.01% to about 20% |
| 259 | *Populas alba* from about 0.01% to about 20% | *Sanguinaria Canadensis* from about 0.01% to about 20% |
| 260 | *Populas alba* from about 0.01% to about 20% | *Scrophularia nodosa* from about 0.01% to about 20% |
| 261 | *Populas alba* from about 0.01% to about 20% | *Smilax medica* from about 0.01% to about 20% |
| 262 | *Populas alba* from about 0.01% to about 20% | *Tussilago farfara* from about 0.01% to about 15% |
| 263 | *Populas alba* from about 0.01% to about 20% | *Veronica officinalis* from about 0.01% to about 15% |
| 264 | *Populas alba* from about 0.01% to about 20% | *Vincetoxicum officinale* from about 0.01% to about 15% |
| 265 | *Populus tremuloides* from about 0.01% to about 20% | *Rhus toxicodendron* from about 0.01% to about 25% |
| 266 | *Populus tremuloides* from about 0.01% to about 20% | *Sambucus nigra* from about 0.01% to about 20% |
| 267 | *Populus tremuloides* from about 0.01% to about 20% | *Sanguinaria Canadensis* from about 0.01% to about 20% |
| 268 | *Populus tremuloides* from about 0.01% to about 20% | *Scrophularia nodosa* from about 0.01% to about 20% |
| 269 | *Populus tremuloides* from about 0.01% to about 20% | *Smilax medica* from about 0.01% to about 20% |
| 270 | *Populus tremuloides* from about 0.01% to about 20% | *Tussilago farfara* from about 0.01% to about 15% |
| 271 | *Populus tremuloides* from about 0.01% to about 20% | *Veronica officinalis* from about 0.01% to about 15% |
| 272 | *Populus tremuloides* from about 0.01% to about 20% | *Vincetoxicum officinale* from about 0.01% to about 15% |
| 273 | *Rhus toxicodendron* from about 0.01% to about 25% | *Sambucus nigra* from about 0.01% to about 20% |

TABLE 1-continued

| No. | Component 1 | Component 2 |
|---|---|---|
| 274 | Rhus toxicodendron from about 0.01% to about 25% | Sanguinaria Canadensis from about 0.01% to about 20% |
| 275 | Rhus toxicodendron from about 0.01% to about 25% | Scrophularia nodosa from about 0.01% to about 20% |
| 276 | Rhus toxicodendron from about 0.01% to about 25% | Smilax medica from about 0.01% to about 20% |
| 277 | Rhus toxicodendron from about 0.01% to about 25% | Tussilago farfara from about 0.01% to about 15% |
| 278 | Rhus toxicodendron from about 0.01% to about 25% | Veronica officinalis from about 0.01% to about 15% |
| 279 | Rhus toxicodendron from about 0.01% to about 25% | Vincetoxicum officinale from about 0.01% to about 15% |
| 280 | Sambucus nigra from about 0.01% to about 20% | Sanguinaria Canadensis from about 0.01% to about 20% |
| 281 | Sambucus nigra from about 0.01% to about 20% | Scrophularia nodosa from about 0.01% to about 20% |
| 282 | Sambucus nigra from about 0.01% to about 20% | Smilax medica from about 0.01% to about 20% |
| 283 | Sambucus nigra from about 0.01% to about 20% | Tussilago farfara from about 0.01% to about 15% |
| 284 | Sambucus nigra from about 0.01% to about 20% | Veronica officinalis from about 0.01% to about 15% |
| 285 | Sambucus nigra from about 0.01% to about 20% | Vincetoxicum officinale from about 0.01% to about 15% |
| 286 | Sanguinaria Canadensis from about 0.01% to about 20% | Scrophularia nodosa from about 0.01% to about 20% |
| 287 | Sanguinaria Canadensis from about 0.01% to about 20% | Smilax medica from about 0.01% to about 20% |
| 288 | Sanguinaria Canadensis from about 0.01% to about 20% | Tussilago farfara from about 0.01% to about 15% |
| 289 | Sanguinaria Canadensis from about 0.01% to about 20% | Veronica officinalis from about 0.01% to about 15% |
| 290 | Sanguinaria Canadensis from about 0.01% to about 20% | Vincetoxicum officinale from about 0.01% to about 15% |
| 291 | Scrophularia nodosa from about 0.01% to about 20% | Smilax medica from about 0.01% to about 20% |
| 292 | Scrophularia nodosa from about 0.01% to about 20% | Tussilago farfara from about 0.01% to about 15% |
| 293 | Scrophularia nodosa from about 0.01% to about 20% | Veronica officinalis from about 0.01% to about 15% |
| 294 | Scrophularia nodosa from about 0.01% to about 20% | Vincetoxicum officinale from about 0.01% to about 15% |
| 295 | Smilax medica from about 0.01% to about 20% | Tussilago farfara from about 0.01% to about 15% |
| 296 | Smilax medica from about 0.01% to about 20% | Veronica officinalis from about 0.01% to about 15% |
| 297 | Smilax medica from about 0.01% to about 20% | Vincetoxicum officinale from about 0.01% to about 15% |
| 298 | Tussilago farfara from about 0.01% to about 15% | Veronica officinalis from about 0.01% to about 15% |
| 299 | Tussilago farfara from about 0.01% to about 15% | Vincetoxicum officinale from about 0.01% to about 15% |
| 300 | Veronica officinalis from about 0.01% to about 15% | Vincetoxicum officinale from about 0.01% to about 15% |

In another non-limiting aspect, disclosed herein are process for obtaining a plant extract, the process comprising the step of a) mixing the plant with water and/or another solvent, b) distilling the mixture, and c) collecting the distillate.

In some embodiments, the process further comprises the step of d) separating the aqueous phase from the oil phase and collecting the aqueous phase, after step c).

In some embodiments, the process further comprises the step of e) adding more of the plant to the aqueous phase and fermenting the mixture, after step c) or after step d).

In some embodiments, the process further comprises the step of f) distilling the fermented mixture and collecting the distillate, after step e).

In some embodiments, the process further comprises the steps of g) heating the remaining plant material until most of the moisture has evaporated, after step f), and h) extracting the water soluble salts or hygroscopic salts from the dried plant material. In some embodiments, the remaining plant material is not completely dry. In other embodiments, the remaining plant material is completely dry. In further embodiments, the remaining plant material begins to char. In yet other embodiments, the remaining plant material begins to incinerate.

In some embodiments, the process further comprises the step of i) adding the distillate of step e) to the extracted salts of step h).

In another non-limiting aspect, disclosed herein are herbal extractions obtained by the above process.

When afflicted with an epidermal condition, the human skin naturally works to alleviate the symptoms of the condition. For example, in most cases, redness, itching, or scaling due to some disorders improve over time, or until the next episode of a flare up. The herbal preparations disclosed herein help the skin in its natural course to reduce the adverse symptoms. Without being bound to a particular theory, the present inventors believe that the present herbal preparations provide the skin with the nutrients and building blocks necessary to efficiently and effectively work to reduce the symptoms.

Thus, in another non-limiting aspect, disclosed herein are methods of reducing symptoms associated with a skin condition in a subject, comprising identifying the subject in need thereof and administering to the subject an effective amount of an herbal preparation as disclosed herein.

In some embodiments, the symptoms associated with a skin condition include, but are not limited to, redness, itching, scaling, flaking, dry skin, acne, and the like associated with disorders such as acne vulgaris, psoriasis, eczema, or atopic dermatitis. In certain embodiments, the skin symptom is pruritis (itching), erythema (redness), or excoriations (flaking).

The term "subject" refers to an animal, such as (but not limited to) a mammal, and more particularly (but not by way of limitation) a human, who is the object of treatment, observation or experiment. The mammal may be selected from the group consisting of mice, rats, rabbits, guinea pigs, dogs, cats, sheep, goats, cows, primates, such as monkeys, chimpanzees, and apes, and humans.

The term "effective amount" or "therapeutically effective amount" is used to indicate an amount of an herbal preparation that elicits the biological response indicated. This response may occur in a tissue, system, animal or human and includes alleviation of the symptoms being treated.

In another non-limiting aspect, disclosed herein are compositions comprising the herbal preparations disclosed herein and at least one physiologically acceptable excipient, diluent, or carrier.

The term "excipient" refers to a substance added to the compositions disclosed herein. In some cases, the herbal preparations disclosed herein may not by itself be easily administered and/or absorbed by the subject. In these cases the herbal preparations may be dissolved into or mixed with an excipient. Excipients are also sometimes used to bulk up formulations that contain the herbal preparations, to allow for convenient and accurate application. In addition to their use in the single application quantity, excipients can be used in the manufacturing process to aid in the handling of the herbal preparations concerned. Excipients also aid in stabilizing the formulations of the herbal preparations, for example by keeping the various ingredients in solution or in suspension, preventing precipitation or crystallization, or adherence to container walls.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of a subject.

The term "diluent" defines chemical compounds diluted in water that will dissolve the herbal extracts of interest and/or stabilize the formulation of the herbal preparations, including shelf life. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the benefit of the herbal preparation.

Accordingly, disclosed herein are compositions and methods for the alleviation of the symptoms of skin conditions. The herbal preparations of the present disclosure can be delivered or administered to a mammal, (e.g., human subject), alone, or in the form of a formulated composition wherein the herbal preparation is mixed with suitable carriers or excipient(s) in an effective amount.

The herbal preparations that are used in the methods disclosed herein can be administered as formulated compositions comprising the herbal preparation together with one or more other physiologically acceptable component. Compositions can be in the form of solids (i.e., powders, granules, dragees, tablets, or pills), semi-solids (i.e., gels, slurries, or ointments), or liquids.

Suitable routes of administration may, for example, include oral, topical, rectal, transmucosal, epidural, vaginal, transdermal, or buccal administration.

Suitable formulations for use in the present disclosure are found in, for example, Remington's Pharmaceutical Sciences, Mack Publishing Company, Philadelphia, PA, 17th ed. (1985) and Langer, Science, 249:1527-1533 (1990). The compositions described herein can be manufactured in a conventional manner, e.g., mixing, dissolving, granulating, dragee-making, levigating, emulsifying, encapsulating, entrapping, or lyophilizing processes.

The herbal preparations can be formulated with common excipients, diluents or carriers, and compressed into tablets, or formulated as elixirs or solutions for convenient oral administration. The agents can also be formulated as sustained release dosage forms and the like.

The compositions disclosed herein may be manufactured in a manner that is itself known, e.g., by means of conventional mixing, dissolving, granulating, dragee-making, levigating, emulsifying, encapsulating, entrapping or tabletting processes.

Compositions for use in accordance with the present disclosure thus may be formulated in a conventional manner using one or more physiologically acceptable carriers comprising excipients and auxiliaries, which facilitate processing of the herbal extracts into herbal preparations. Proper formulation is dependent upon the route of administration chosen. Any of the well-known techniques, carriers, and excipients may be used as suitable and as understood in the art; e.g., in Remington's Pharmaceutical Sciences, above.

For transmucosal administration, penetrants appropriate to the barrier to be permeated are used in the formulation. Such penetrants are generally known in the art.

Compositions suitable for use in accordance with the present disclosure include compositions wherein the herbal preparations are contained in an effective amount. The effective amounts for the methods of the present disclosure can depend on a variety of factors, including, e.g., age, body weight, general health, sex, diet, time and manner of administration, and the severity of the particular affliction being treated.

EXAMPLES

Example 1: Herb Extraction

Procedure A

Herb extraction was achieved by steam distillation. Optionally, one or more of the steps of oil separation, fermentation, hygroscopic salt extraction, and cohobation was added to the steam distillation step. The procedures were as follows.

Steam Distillation

Three liters of deionized water was poured into a 5 L distillation apparatus flask, which was then placed on a sand bath. Herb was added to the distillation apparatus flask until the flask was about half full. A filter paper was placed at the joint of the distillation apparatus before hooking up the reaction head adaptor. A 2 L receiving flask was used. Low heat was provided, sufficient for steam to cloud the distillation apparatus and adapter. After 1.5 L of distillate was collected, the heat was turned off and the apparatus was allowed to cool. The distillate was removed. One liter of deionized water was added to the distillation apparatus flask and the distillation was repeated. The distillation was repeated three times.

Oil Separation

The distillate, containing an aqueous phase and an oil phase, was transferred into a foil drain tube. The stopcock at the end of the drain tube was opened and the water was drained off into a 5 L flask.

Fermentation

Herb was placed into the 5 L flask containing the water after oil separation. The flask was sealed using a secure fermentation lock, and was incubated at 27° C. for two weeks. Subsequently, the water was distilled 5 times and the distillate was saved in a separate container.

Hygroscopic Salt Extraction

The remaining plant material was boiled until the moisture was evaporated and the plant material began to incinerate. Once the incinerated plant material became grey, it was removed from heat and allowed to cool. A Soxhlet extractor was used to extract the water soluble salts from the incinerated plant material. The salts were isolated by rotary evaporation. The extracted salts were placed in a calcining kiln at 600° C. for 1 week. The process was repeated for a total of 3 times.

Cohobation

The solution obtained after fermentation and the volatile oils were added to the isolated salts. The mixture was incubated at 30° C. for 1 week. The herbal-medicinal concentrate was separated without disturbing the sediment. The concentrate can be diluted as needed.

Procedure B

Each individual plant raw material was subjected to steam distillation. After distillation the leftover material was in the form of wet mass. Additional water was added and the mixture was allowed to ferment in a glass container covered with a cloth lid. Fermentation was continued for 7 days at room temperature. During the fermentation the pH was monitored. Fermentation was allowed to continue until the mixtures began to putrefy. After the fermentation was over the biomass was filtered through a cloth filter and was subjected to distillation at 80-90° C. to get 30-40% of distillate of filtrate.

The leftover biomass was transferred to trays made from GI/MS and covered with cloth and was kept for drying in the shade. The drying was continued until the biomass became crisp dry, i.e., for about 15-20 days. During this time the material was turned around once in a day. After drying the material was subjected to ashing by either 1) burning the dry mass and collecting the cooled ash, which was then transferred to a crucible and heated further in an oven, or 2) incinerating the biomass by heating in a crucible at 600° C. The ash obtained is dissolved in distilled water and subjected to further distillation. All distillates were combined together and subjected to cohobation, where the combined product is heated under reflux for some time.

Example 2: Herbal Preparations

For the experiments detailed below, a unique herbal preparation (HAT-01) was used. Table 2 shows the herbs and their weight percentages within this formulation.

TABLE 2

Composition of HAT-01

| Genus | Species | Common Name | Percentage Composition |
|---|---|---|---|
| Conium | maculatum | Hemlock | 12.1 |
| Hamamelis | virginiana | Witch hazel | 8.9 |
| Rhus | toxicodendron | Ivy | 8.3 |
| Avena | sativa | Oat | 6.8 |
| Hydrastis | canadensis | Orange root | 6.0 |
| Phytolacca | decandra | Poke root | 5.8 |
| Cochlearia | officinalis | Scurvy grass | 5.1 |
| Populus | alba | White Poplar | 4.9 |
| Populus | tremuloides | Quaking Aspen | 4.8 |
| Sanguinaria | canadensis | Blood root | 4.5 |
| Berberis | vulgaris | Barberry | 4.1 |
| Scrophularia | nodosa | Figwort | 4.0 |
| Ervum | lens | Lentil | 3.7 |
| Smilax | medica | Sarsaparilla | 3.1 |
| Achillea | millefolium | Yarrow | 2.5 |
| Aesculus | hippocastanum | Horsechestnut | 2.4 |
| Capsella | Bursa Pastoris | Shepherd's Purse | 2.3 |
| Matricaria | chamomilla | Chamomile | 2.2 |
| Althaea | officinalis | Mallow | 2.0 |
| Sambucus | nigra | Elderberry | 1.9 |
| Pimpinella | saxifraga | Burnet | 1.1 |
| Vincetoxicum | officinale | Swallow wort | 0.9 |
| Nasturtium | officinale | Watercress | 0.9 |
| Tussilago | farfara | Colts foot | 0.9 |
| Veronica | officinalis | Speedwell | 0.8 |
| | | Total | 100 |

Furthermore, to compare constituent efficacy and synergism, HAT-01 was also partially formulated into two: HAT-01:P1 and HAT-01:P2 as described in Tables 3 and 4, respectively. These herbs have established clinical benefit, and are considered safe for clinical use in chronic inflammatory conditions.

TABLE 3

Composition of HAT-01:P1

| Genus | Species | Percentage Composition |
|---|---|---|
| Conium | maculatum | 21 |
| Rhus | toxicodendron | 17 |
| Cochlearia | officinalis | 10 |
| Hydrastis | canadensis | 8 |
| Phytolacca | decandra | 8 |
| Berberis | vulgaris | 8 |
| Scrophularia | nodosa | 8 |
| Smilax | medica | 6 |
| Matricaria | chamomilla | 4 |
| Pimpinella | saxifraga | 2 |
| Vincetoxicum | officinale | 2 |
| Nasturtium | officinale | 2 |
| Tussilago | farfara | 2 |
| Veronica | officinalis | 2 |
| | Total | 100 |

TABLE 4

Composition of HAT-01:P2

| Genus | Species | Percentage Composition |
|---|---|---|
| Hamamelis | virginiana | 13 |
| Avena | sativa | 14 |
| Populus | alba | 10 |
| Populus | tremuloides | 10 |

TABLE 4-continued

Composition of HAT-01:P2

| Genus | Species | Percentage Composition |
|---|---|---|
| Sanguinaria | canadensis | 9 |
| Ervum | lens | 8 |
| Achillea | millefolium | 5 |
| Aesculus | hippocastanum | 5 |
| Hydrastis | canadensis | 5 |
| Capsella | Bursa Pastoris | 5 |
| Althaea | officinalis | 4 |
| Conium | maculatum | 4 |
| Phytolacca | decandra | 4 |
| Sambucus | nigra | 4 |
| | Total | 100 |

Our NMR analyses of the ingredients in HAT-01 have confirmed the relative concentrations of components, and absolute concentrations of known substances. Of note, results from 1H-NMR spectroscopic analyses of HAT-01 showed no evidence of a corticosteroid moiety, which correlates well with our findings that no changes were observed in serum cortisol levels in mice before and after treatment with 10% oral HAT-01, and demonstrating that HAT-01 effects are nonsteroidal.

Example 3: Benefits of HAT-01 in Patients with Psoriasis: Pilot Trial

To assess the benefits of HAT-01 in psoriasis, we performed an 8-week, open-label, two armed study (HAT-01 and OTC medication arm) in patients with mild to moderate chronic plaque psoriasis. Patients (aged 18 to 70 years) with stable chronic plaque psoriasis of at least 6 months duration with a psoriasis body surface area (BSA)≤10% were included. All areas with the exception of the face, groin and axillae were treated. Patients with current or recent malignancies, severe asthma, infections, uncontrolled hypertension, and/or those treated with systemic or topical corticosteroid or immunosuppressant agents were excluded from the study. Patients with abnormal screening laboratory values, as well as pregnant women, were also excluded from the study. Patients were not allowed to use any medicated cosmetics that might influence the outcome of the study. A total of 16 patients fulfilling psoriasis inclusion criteria were enrolled into an exploratory 8 week, open-label study designed to investigate the safety, utility and tolerability of HAT-01. Patients were enrolled into one of two arms: (a) twice-daily application of HAT-01 (n=9 patients) or (b) twice-daily application of over-the-counter topical medications which are first-line therapy for patients with psoriasis and included topical vitamin D3 analog calcipotriene or topical retinoids (n=7 patients). Approximately 300 µl of HAT-01 was applied per lesion, prepared as a 10% dilution of the concentrated herbal extracts in 4.9% EtOH. The primary outcome was defined as the percentage change from baseline in the body surface area affected by psoriasis at weeks 2, 4, and 8 following treatment. Safety evaluations included tolerability assessments and incidence of adverse events.

Patients were evaluated for changes in total body surface area, erythema, scaling, and plaque resolution. Patients with moderate disease activity who received HAT-01 demonstrated an average 42% reduction in the percentage in body surface area affected by psoriasis at 8 weeks, whereas those treated with a control OTC topical vitamin D3 analog calcipotriene and topical retinoids exhibited a reduction in the percentage in body surface area affected by psoriasis by only 12% (FIG. 1). Significant resolution in erythema and scaling with changes in plaque elevation (from that of marked to slight) was observed in 8 of 9 patients after 8 weeks of HAT-01 treatment.

HAT-01 was well tolerated, with no treatment-related adverse events observed throughout the 8-week trial. At week 8, all patients treated with HAT-01 had no reports of skin atrophy, pruritus, or burning/stinging. In contrast at 8 weeks of treatment, 4 of 7 patients that were treated with control OTC topical vitamin D3 analog calcipotriene exhibited local treatment-site irritation, burning sensation, and pain.

Example 4: Therapeutic Effects of HAT-01 in Patients with Acne Vulgaris: Clinical Vignettes To assess the effects of HAT-01 in acne vulgaris, an open-label study of HAT-01 in subjects with mild to moderate (grade I and II) acne vulgaris was undertaken at an outpatient setting of a private practice clinic. Subjects aged 18 to 50 years of age with ≥three inflammatory or non-inflammatory lesions of papules or pustules in the face were included. Exclusion criteria included: severe acne, the use of any anti-acne medications within the preceding four weeks, or subjects with cystic lesions or any acne requiring systemic treatment. Subjects were not allowed to use any medicated cosmetics that might influence the outcome of the study. A total of 4 patients fulfilling criteria were enrolled. The primary efficacy outcome was defined as the change from baseline of the total lesion count. Subjects were asked to follow a 4 week regimen of twice daily applications of HAT-01 (300 µl applied per lesion, prepared as a 10% dilution of the concentrated herbal extracts in 4.9% EtOH). An analysis of the post-treatment inflammatory and non-inflammatory lesion counts demonstrated a highly significant reduction of scores from baseline to 4 week time points, indicative of the therapeutic potential of HAT-01 in acne vulgaris. HAT-01 was well tolerated, with no treatment-related adverse events observed throughout the 4-week trial including no reports of skin atrophy, pruritus, or burning/stinging at the local treatment-site.

Example 5: Clinical Studies

Methodology

The clinical trial was conducted in a contract research organization setting with three investigators (dermatologists) in a multi-center site. Patients were block randomized from a central location into each study arm. Patients were assessed both before and throughout the course of treatment at each visit using by SCORAD and a Patient Benefit Index (which assesses AD patient-relevant treatment benefit). SCORAD values, ranging from 0 to 103, are classified as mild (<15), moderate (16-40) and severe (>41), and are calculated as (0.2×Area)+(3.5×Erythema+Edema+Crust+Excoriation+Lichenification+Dryness)+(pruritus+sleep loss). All three investigators were given prior training and testing for standardized scoring of SCORAD in AD, an approach that has been found to be significantly beneficial for minimizing observer variability.

Our primary objective was the efficacy of HAT-01, HAT-01P1, and/or HAT-01P2 in the reduction of pruritus in atopic dermatitis patients.

Our secondary objective(s) were to
evaluate the therapeutic benefit of HAT-01, HAT-01P1, and/or HAT-01P2 in atopic dermatitis as measured by the SCORAD (SCORing Atopic Dermatitis),
evaluate the therapeutic benefit of HAT-01, HAT-01P1, and/or HAT-01P2 to reduce pruritus from patient's perspective as assessed by the Patient Benefit Index, and
safety and tolerability of HAT-01, HAT-01P1, and/or HAT-01P2 in atopic dermatitis patients.

Double Blinded Randomization: A double blind approach where both investigators and patients are blinded was used. Investigators performed enrollment and blinded assignment using blinded labels. Assignments were rotated through enrollment by investigators to enable random continuous enrollment and avoid selection bias.

Treatment: Atopic dermatitis patients fulfilling eligibility (inclusion and exclusion criteria) were provided with an informed consent. A topical formulation of HAT-01, HAT-01P1, and/or HAT-01P2 was randomly and blindly provided (without patient knowledge) and followed through 2, 4, 8, and 12 weeks after treatment. Patients were assessed both before and throughout the course of treatment (each visit) for the following indices: SCORAD (SCORing Atopic Dermatitis), Patient Benefit Index. Each patient also had up to 10 mls of blood drawn prior to (0) and at 4, and 12, weeks post-therapy to distinguish laboratorial and cytokine changes over time. Serum from 64 patients with AD on an approved randomized single blind placebo-controlled clinical trial of HAT-01, placebo and partial formulations of HAT-01 were obtained for all groups at 3 time points (0, 4, 12 weeks).

Therapeutic Effects of HAT-01 in Patients with Atopic Dermatitis: Pilot Trial

Figure 2:
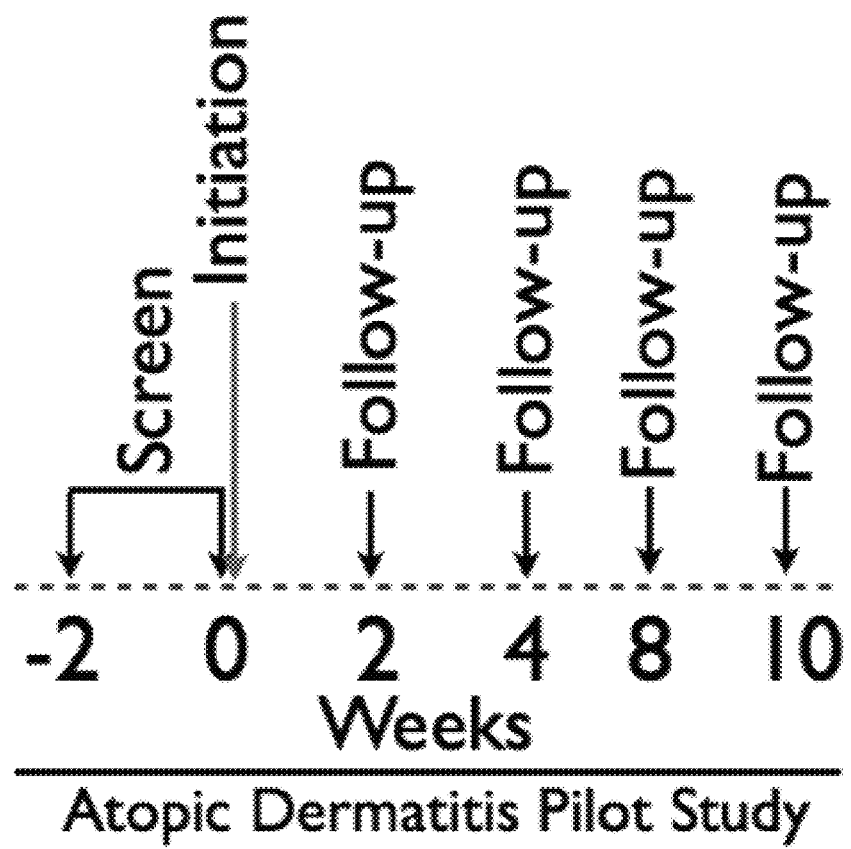
FIG. 2 is an illustration of the pilot trial study design conducted to evaluate the safety, benefit & tolerability of HAT-01 in patients with atopic dermatitis FIG. 3 demonstrates the benefit of HAT-01 in a study of patients with atopic dermatitis.
Figure 3:
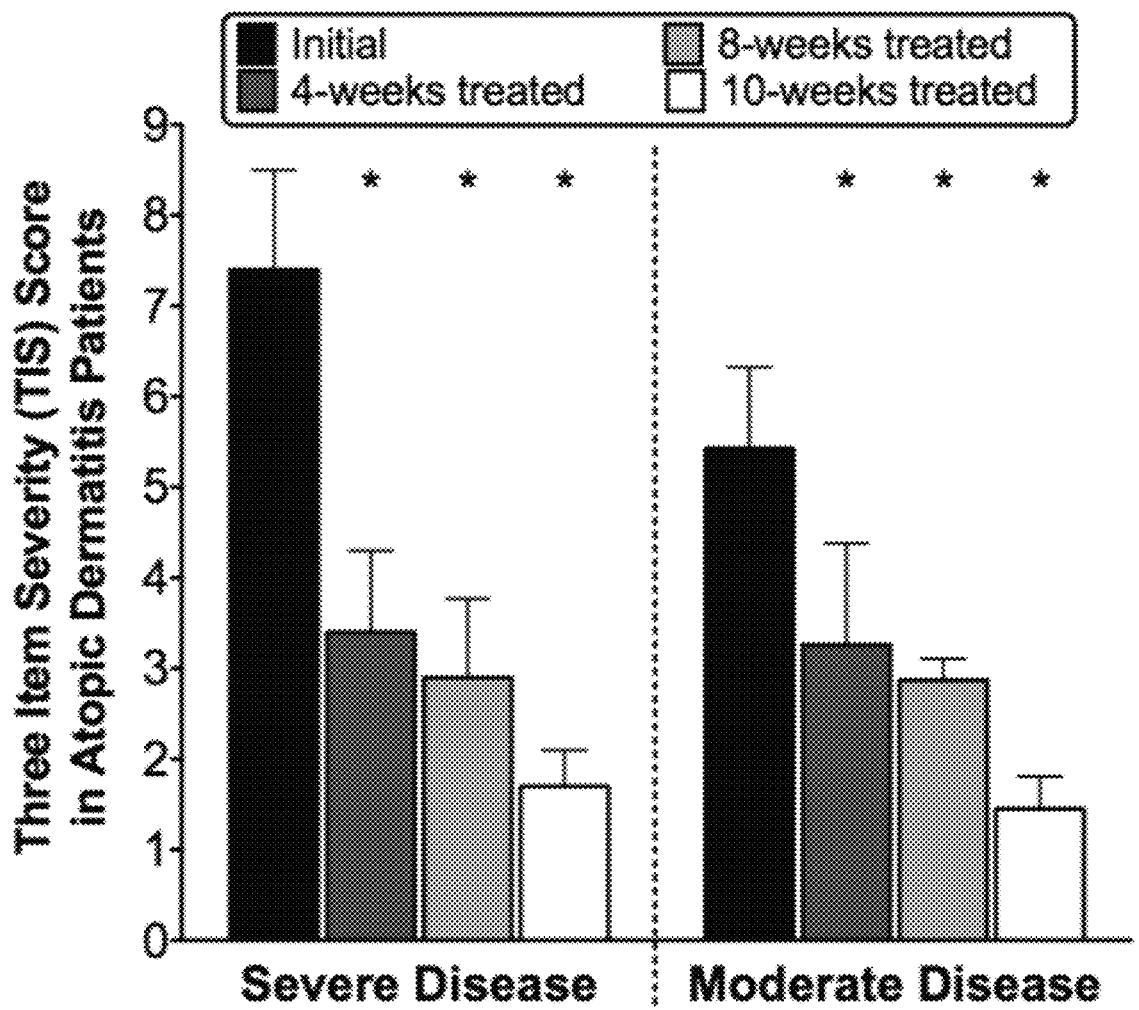

To correlate our findings in human patients with AD, we performed an exploratory 10-week, open-label study to evaluate the utility of HAT-01 in atopic dermatitis. Significant resolution of symptoms and signs of AD was observed through a Three Item Severity score in 15 of 18 patients after 4 weeks of topical HAT-01 treatment, with no relapses at 10-weeks of follow up. We then performed pilot clinical studies to evaluate the utility of HAT-01 in atopic dermatitis. Patients with severe asthma and/or those treated with systemic or topical (greater than medium strength) corticosteroids or immunosuppressant agents were excluded from the study. An exploratory 10-week, open-label study was designed to investigate the safety, efficacy and tolerability of a twice-daily application of a topical formulation of HAT-01 in AD. A total of 18 patients fulfilling diagnostic criteria for AD were enrolled and placed on a regimen of twice daily application of a topical formulation of HAT-01 (300 µl of 1:10). FIG. 2 portrays the design outline of this pilot trial. The primary efficacy outcome was defined as the change in the Three Item Severity score (TIS score) of AD based on the evaluation of erythema, oedema/papulation and excoriation in each representative lesion. Significant resolution of symptoms and signs of AD was observed in 83% of patients (15 of 18) after 4 weeks of HAT-01 treatment, with no relapses at 8-week or 10-week follow up (FIG. 3). Patients with severe disease activity pretreatment (TIS score>6) demonstrated an average 54.6% reduction in disease activity at 4-weeks, and an average of 77.1% reduction in disease activity by 10-weeks (FIG. 3). Of note, a significant reduction in edema and erythema was observed within 2-weeks, which was followed by improvements in oozing and excoriations within 4 weeks following treatment with HAT-01. Significant improvement in xerosis (dryness) was also immediately observed, while improvement in lichenification (thickening) took up to 10 weeks for effective resolution.

Figure 4:
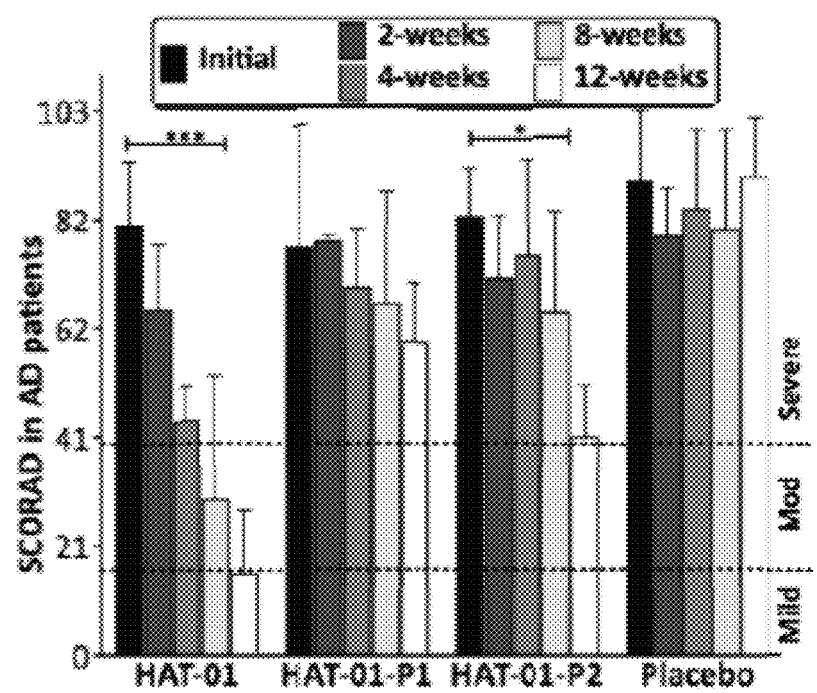
FIG. 4 illustrates the benefit of HAT-01 in a study in patients with atopic dermatitis.

AD: Therapeutic effects of HAT-01 in patients with atopic dermatitis: Randomized placebo-controlled trial. To further investigate the safety, efficacy and tolerability of a twice-daily application of a topical formulation of HAT-01 in atopic dermatitis (AD), a total of 64 patients fulfilling inclusion criteria for AD were enrolled into a randomized placebo-controlled single (patient) blind clinical trial with a regimen of twice daily application of a topical formulation of HAT-01 (300 µl of 1:10). The primary efficacy outcome was defined as the change in the Severity Scoring of Atopic Dermatitis (SCORAD) values. SCORAD values, ranging from 0 to 103, are classified as mild (<15), moderate (16-40) and severe (>41), and are calculated as (0.2×Area)+(3.5×Erythema+Edema+Crust+Excoriation+Lichenification+Dryness)+(pruritis+sleep loss). As shown in FIG. 4, significant resolution of symptoms and signs of AD was observed in 84% of patients after 4 weeks of HAT-01 treatment, with sustained effects and no relapses at 8-week or 12-weeks of follow up (FIG. 4). Placebo (vehicle) treatment had no significant effect on SCORAD values, and treatment with partial formulations HAT-01:P1 and HAT-01:P2 had only minimal effects relative to treatment with whole HAT-01 (FIG. 4). Significant reduction in edema and erythema was observed within 4-weeks, which was followed by improvements in oozing and excoriations within 8 weeks following treatment with HAT-01. Significant improvement in xerosis was also observed at 4 weeks, while improvement in lichenification took up to 12 weeks for effective resolution. Importantly, HAT-01 was well tolerated and no treatment-related adverse events were observed throughout the 12-week pilot trial, indicating the safe and potent therapeutic benefit of HAT-01 in a majority of the patients studied with AD.

What is claimed is:

1. A method of reducing symptoms associated with a skin condition in a subject, wherein the skin condition is associated with acne vulgaris, psoriasis, eczema, atopic dermatitis, pruritis, erythema, or excoriations, the method comprising the steps of:
   identifying the subject in need thereof; and
   applying an effective amount of a topical composition to a skin of the subject, wherein the topical composition is in the form of a cream, gel, lotion, ointment, or salve for application to the skin of the subject, and wherein the topical composition comprises:
      a mixture of at least seven different plant extracts, wherein each of the at least seven plant extracts is selected from the group consisting of *Achillea millefolium; Aesculus hippocastanum; Althaea officinalis; Avena sativa; Berberis vulgaris; Capsella bursa-pastoris; Cochlearia officinalis; Conium maculatum; Ervum lens; Hamamelis virginiana; Hydrastis canadensis; Malva sylvestris; Matricaria chamomilla; Nasturtium officinale; Phytolacca decandra; Pimpinella saxifraga; Populus alba; Populus tremuloides; Rhus toxicodendron; Sambucus nigra; Sanguinaria canadensis; Scrophularia nodosa; Smilax medica; Tussilago farfara; Veronica officinalis; Vincetoxicum officinale*; and combinations thereof; and wherein each of the at least seven different plant extracts is extracted in an extraction composition that comprises at least one solvent other than water, and wherein each of the at least seven different plant extracts is extracted by a process selected from the group consisting of steam distillation, oil separation, fermentation, hygroscopic salt extraction, and cohobation; and at least one pharmaceutically acceptable carrier, diluent, or excipient.

2. The method of claim 1, wherein the mixture of the topical composition comprises at least eight different plant extracts.

3. The method of claim 1, wherein the mixture of the topical composition comprises at least ten different plant extracts.

4. The method of claim 1, wherein the mixture of the topical composition comprises at least twelve different plant extracts.

5. The method of claim 1, wherein the mixture of the topical composition comprises at least fourteen different plant extracts.

6. The method of claim 1, wherein the mixture of the topical composition comprises at least sixteen different plant extracts.

7. The method of claim 1, wherein the mixture of the topical composition comprises at least eighteen different plant extracts.

8. The method of claim 1, wherein the mixture comprises plant extracts obtained from *Achillea millefolium; Aesculus hippocastanum; Althaea officinalis; Avena sativa; Berberis vulgaris; Capsella Bursa Pastoris; Cochlearia officinalis; Ervum lens; Hamamelis virginiana; Malva sylvestris; Matricaria chamomilla; Nasturtium officinale; Phytolacca decandra; Pimpinella saxifraga; Populas alba; Populus tremuloides; Sambucus nigra; Sanguinaria Canadensis; Scrophularia nodosa; Smilax medica; Tussilago farfara; Veronica officinalis;* and *Vincetoxicum officinale.*

9. The method of claim 1, wherein the at least one solvent present in the extraction composition utilized with at least one of the plant extracts is selected from the group consisting of an alcohol, a polyhydric alcohol, an ether, an ester, a carboxylic acid, an amide, a carbonate, supercritical fluid carbon dioxide, an ionic liquid, an alkane, a petroleum-derived oil, a plant oil, and combinations thereof.

10. The method of claim 9, wherein the at least one solvent comprises ethanol.

11. The method of claim 1, wherein the extraction composition further comprises water.

12. The method of claim 1, wherein the topical composition is formulated as a sustained release dosage form.

* * * * *